(12) United States Patent
Hawkes et al.

(10) Patent No.: US 11,266,447 B2
(45) Date of Patent: Mar. 8, 2022

(54) SURGICAL CONSTRUCTS AND RELATED METHODS OF INSTALLATION

(71) Applicant: Nexus Spine, L.L.C., Salt Lake City, UT (US)

(72) Inventors: David T. Hawkes, Pleasant Grove, UT (US); Quentin T. Aten, Draper, UT (US)

( * ) Notice: Subject to any disclaimer, the term of this patent is extended or adjusted under 35 U.S.C. 154(b) by 383 days.

(21) Appl. No.: 14/555,573

(22) Filed: Nov. 26, 2014

(65) Prior Publication Data

US 2015/0148853 A1 May 28, 2015

Related U.S. Application Data

(60) Provisional application No. 61/909,217, filed on Nov. 26, 2013.

(51) Int. Cl.
*A61B 17/70* (2006.01)

(52) U.S. Cl.
CPC ...... *A61B 17/7083* (2013.01); *A61B 17/7001* (2013.01); *A61B 17/7007* (2013.01); *A61B 17/7076* (2013.01); *A61B 17/7079* (2013.01); *A61B 17/704* (2013.01); *A61B 17/705* (2013.01)

(58) Field of Classification Search
CPC ............ A61B 17/7074; A61B 17/7076; A61B 17/7091; A61B 17/7082; A61B 17/7086; A61F 2/4637
See application file for complete search history.

(56) References Cited

U.S. PATENT DOCUMENTS

| | | | |
|---|---|---|---|
| 5,139,499 A * | 8/1992 | Small | A61B 17/864 606/104 |
| 6,270,529 B1 | 8/2001 | Terrill-Grisoni et al. | |
| 7,988,698 B2 * | 8/2011 | Rosenberg | A61B 17/7086 606/265 |
| 8,454,658 B2 * | 6/2013 | Lindner | A61B 17/7041 606/246 |
| 8,709,049 B2 * | 4/2014 | Klein | A61B 17/7007 606/259 |
| 9,615,862 B1 * | 4/2017 | Doubler | A61B 17/7076 |
| 2004/0147936 A1 * | 7/2004 | Rosenberg | A61B 17/7086 606/99 |

(Continued)

FOREIGN PATENT DOCUMENTS

| EP | 1741396 A1 | 1/2007 |
|---|---|---|
| EP | 2574297 A1 | 4/2013 |

*Primary Examiner* — Lynnsy M Summitt
(74) *Attorney, Agent, or Firm* — Adam D. Stevens; Kirton McConkie

(57) ABSTRACT

A method of assembling a surgical construct includes installing a fastener within a bone of a patient. A connector rod is positioned on the fastener and an interference or press fit is created between the fastener and the rod, with very little effort required on the surgeon's part. No additional steps are necessary or desirable; the surgeon can simply position the rod over the fastener, and very quickly and accurately couple the two one to another. A securing device can be used to couple the fastener and the rod, and a different device can be used to uncouple the fastener from the rod. The securing device engages the fastener and the rod, and pushes the rod over the fastener as the surgeon activates the gripping mechanism.

20 Claims, 29 Drawing Sheets

(56) References Cited

U.S. PATENT DOCUMENTS

| | | | |
|---|---|---|---|
| 2008/0195155 A1* | 8/2008 | Hoffman | A61B 17/7091 |
| | | | 606/278 |
| 2008/0228233 A1* | 9/2008 | Hoffman | A61B 17/7088 |
| | | | 606/86 A |
| 2010/0198268 A1 | 8/2010 | Zhang et al. | |
| 2011/0276098 A1* | 11/2011 | Biedermann | A61B 17/7074 |
| | | | 606/305 |
| 2013/0110123 A1 | 5/2013 | Foirella et al. | |
| 2016/0143672 A1* | 5/2016 | Black | F16B 25/001 |
| | | | 29/283 |

* cited by examiner

SURGICAL CONSTRUCTS AND RELATED METHODS OF INSTALLATION

CROSS-REFERENCE TO RELATED APPLICATIONS

This application claims the benefit of U.S. Provisional Application No. 61/909,217, filed Nov. 26, 2014. The present technology is related to U.S. patent application Ser. No. 12/711,131, U.S. patent application Ser. No. 13/455,854, U.S. patent application Ser. No. 11/952,709, and U.S. patent application Ser. No. 14/060,753, all of which are hereby incorporated herein by reference in their entirety. To the extent any teachings in these previous applications are inconsistent with the present application, these previous applications are to be considered subordinate to the teachings herein.

BACKGROUND OF THE INVENTION

1. Field of the Invention

The present invention relates to generally to the field of coupling systems for use in surgical implants, and more particularly to systems and methods for installing components of such systems during surgical procedures.

2. Background and Related Art

The use of bone stabilization/fixation devices to align or position bones is well established. Furthermore, the use of spinal bone stabilization/fixation devices to align or position specific vertebrae or a region of the spine is well established. Typically such devices use a coupling assembly to connect or link two or more surgical screws and/or pedicle screws together to stabilize the bone and/or joint around which the screws are fixed. The coupling assembly typically is comprised of a relatively rigid member such as a plate or a rod that is used to couple or join adjacent structures or parts of the anatomy. Once the coupled structures are spatially fixed in position, procedures can be completed, healing can proceed, and the like.

Conventional surgical and/or pedicle screw coupling systems, however, have several drawbacks. Those coupling systems are rather large and bulky, which can result in more tissue damage in and around the surgical site, both from when the coupling system is installed during surgery and from implant induced, post-operative tissue irritation and erosion. The relative bulk of the prior art devices may be particularly relevant in supra-fascial applications. The prior art coupling systems have a rod-receiving device that is delivered to the surgeon already coupled or attached to the head of the surgical screw, which poses two challenges: 1) this prevents certain surgical maneuvers (e.g. placing the screws prior to interbody work); and, 2) increases the carrying cost of the inventory. Further, with traditional systems there is an inability to easily extend a fusion; that is to say that in a revision procedure the existing rod would need to be removed rather than just adding a short rod segment to the end of the coupling system. In addition, some of the prior art coupling systems include locking components (e.g., set screws and the like) that must all be carefully assembled together during the surgical procedure. Further, many traditional surgical screw system designs preclude the ability to be placed percutaneously over a guide wire, which makes these systems more difficult to install and maneuver during surgical procedures, including minimally invasive procedures.

Moreover, prior art devices require that the rod be assembled to the coupling device after the screw is inserted in the bone, which can be disadvantageous at times, whereas the option to assemble the rod to the coupling device outside the wound may prove valuable. Also, existing coupling systems necessitate simultaneous locking of all components, which prevents the ability to properly compress a coupling system along the rod because the angle relative to the surgical screw would change. Yet further still, to accommodate various anatomies and/or misplacement of surgical screws due to simple tolerance variances and/or error, requires a surgeon to bend the rod, thus further increasing cost and complexity. An example of such a prior art surgical screw system is disclosed in U.S. Pat. Publ. No. 2008/0140075, titled Press-On Pedicle Screw System, which has a common inventor with this application and is owned by the assignee of this application.

Thus, there exists a need for a coupling system for surgical screws that accommodates and allows for misalignment and/or varying tolerances and/or differing anatomies and/or geometries. There also exists a need for a coupling system or assembly that is smaller in profile than existing coupling systems, which may be particularly applicable to supra-fascial placement. There is a need for coupling systems better adapted for use over a guide wire, and with minimally invasive surgical techniques, such as endoscopy. There also exists a need for a coupling system that comprises fewer components (e.g., no set screws), has a lower profile, and accommodates easier assembly and/or disassembly in-situ (i.e., within the patient) and before implantation than existing coupling systems. This includes the ability to assemble the rod to the coupling/connecting device prior to placement in the surgical wound. There is a need for a system that provides for simple extension of a coupling system in revision surgery. There is a need to decrease the carrying cost of inventory by eliminating the requirement of placing a connecting-device on each pedicle screw prior to implantation.

BRIEF SUMMARY OF THE INVENTION

According to implementations of the invention, various surgical constructs are provided, along with devices and methods for installing such constructs. According to implementations of the invention, a device for performing an action selected from the group consisting of coupling a surgical construct to a pedicle screw and uncoupling a surgical construct from a pedicle screw is provided. The device includes a body comprising a handle at a proximal end thereof, a rod running through the body, a trigger connected to the rod through a linkage, and a construct-engaging tip adapted to secure against distal movement a component of a surgical construct selected from the group consisting of a pedicle screw and a body adapted to be coupled to a pedicle screw. Actuating the trigger causes the rod to move within the body toward the construct-engaging tip such that a distal end of the rod protrudes from the body a distance sufficient to apply a force to a first component of the surgical construct while the construct-engaging tip applies a directionally opposite force to a second component of the surgical construct.

The construct-engaging tip may include an open-sided aperture sized to accept a shaft of a pedicle screw therethrough. The distal end of the rod may include a surgical construct retaining feature. The surgical construct retaining feature may include a rigid post surrounded by a plurality of flexible segments. The construct-engaging tip may be adapted to secure a head of a pedicle screw. The rod may be adapted to apply force to a tulip body of a surgical construct to thereby couple the tulip body to the head of the pedicle screw via a press fit.

The construct-engaging tip may alternatively be adapted to secure a tulip body of a surgical construct. The rod may be adapted to apply force to a head of a pedicle screw to thereby uncouple the tulip body from the head of the pedicle screw. The construct-engaging tip may be adapted to secure a tulip head of a surgical construct. The rod may be adapted to apply force to a head of a pedicle screw to thereby couple the tulip body to the head of the pedicle screw via a press fit. The rod may be cannulated.

According to implementations of the invention, a method is provided for coupling a surgical construct to a pedicle screw. The method may include steps of temporarily affixing and retaining a first coupler segment of a body of a surgical construct to a locker device, using a screw-engaging tip of the locker device to engage underneath a spherical head of a first pedicle screw while simultaneously positioning the first coupler segment of the body of the surgical construct over the spherical head of the first pedicle screw, and actuating the locker device to drive the first coupler segment of the body down onto the spherical head of the first pedicle screw, thereby creating an interference fit between the first coupler segment of the body and the spherical head of the first pedicle screw.

The method may also include using the screw-engaging tip of the locker device to engage underneath a spherical head of a second pedicle screw, with a second coupler segment of the body of the surgical construct being positioned over the spherical head of the second pedicle screw, and actuating the locker device to drive the second coupler segment of the body down onto the spherical head of the second pedicle screw, thereby creating an interference fit between the second coupler segment of the body and the spherical head of the second pedicle screw.

Actuating the locker device to drive the second coupler segment of the body down onto the spherical head of the second pedicle screw may include applying distraction between the first pedicle screw and the second pedicle screw. Actuating the locker device to drive the second coupler segment of the body down onto the spherical head of the second pedicle screw may include applying compression between the first pedicle screw and the second pedicle screw. Actuating the locker device to drive the second coupler segment of the body down onto the spherical head of the second pedicle screw may include applying reduction between the first pedicle screw and the second pedicle screw. The method may be adapted to be performed after the first pedicle screw is embedded in a substrate.

According to further implementations of the invention, a method is provided for coupling a surgical construct to a pedicle screw. The method may include steps of inserting a screw ball into a first coupler segment of a body of a surgical construct, inserting a generally cylindrical head of a first pedicle screw into the screw ball within the first coupler segment of the body to create an assembled screw ball-first pedicle screw assembly, using a body-engaging tip of a locker device to engage underneath the first coupler segment of the body, and actuating the locker device to drive the assembled screw ball-first pedicle screw assembly down in the first coupler segment of the body, thereby creating an interference fit between the first coupler segment of the body and the screw ball-first pedicle screw assembly.

The method may also include inserting a screw ball into a second coupler segment of the body of the surgical construct, inserting a generally cylindrical head of a second pedicle screw into the screw ball within the second coupler segment of the body to create an assembled screw ball-second pedicle screw assembly, using the body-engaging tip of the locker device to engage underneath the second coupler segment of the body, and actuating the locker device to drive the assembled screw ball-second pedicle screw assembly down in the second coupler segment of the body, thereby creating an interference fit between the second coupler segment of the body and the screw ball-second pedicle screw assembly.

Actuating the locker device to drive the assembled screw ball and second pedicle screw assembly down in the second coupler segment of the body may include applying distraction between the first pedicle screw and the second pedicle screw. Actuating the locker device to drive the assembled screw ball and second pedicle screw assembly down in the second coupler segment of the body may include applying compression between the first pedicle screw and the second pedicle screw. The method may be adapted to be performed after the first pedicle screw is embedded in a substrate. The method may further include using a body-engaging tip of an unlocker device to engage underneath the first coupler segment of the body and actuating the unlocker device to drive the screw ball-first pedicle screw assembly down in the first coupler segment of the body until the screw ball-first pedicle screw assembly is forced out of the first coupler segment of the body, thereby uncoupling the body from the screw ball-first pedicle screw assembly.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
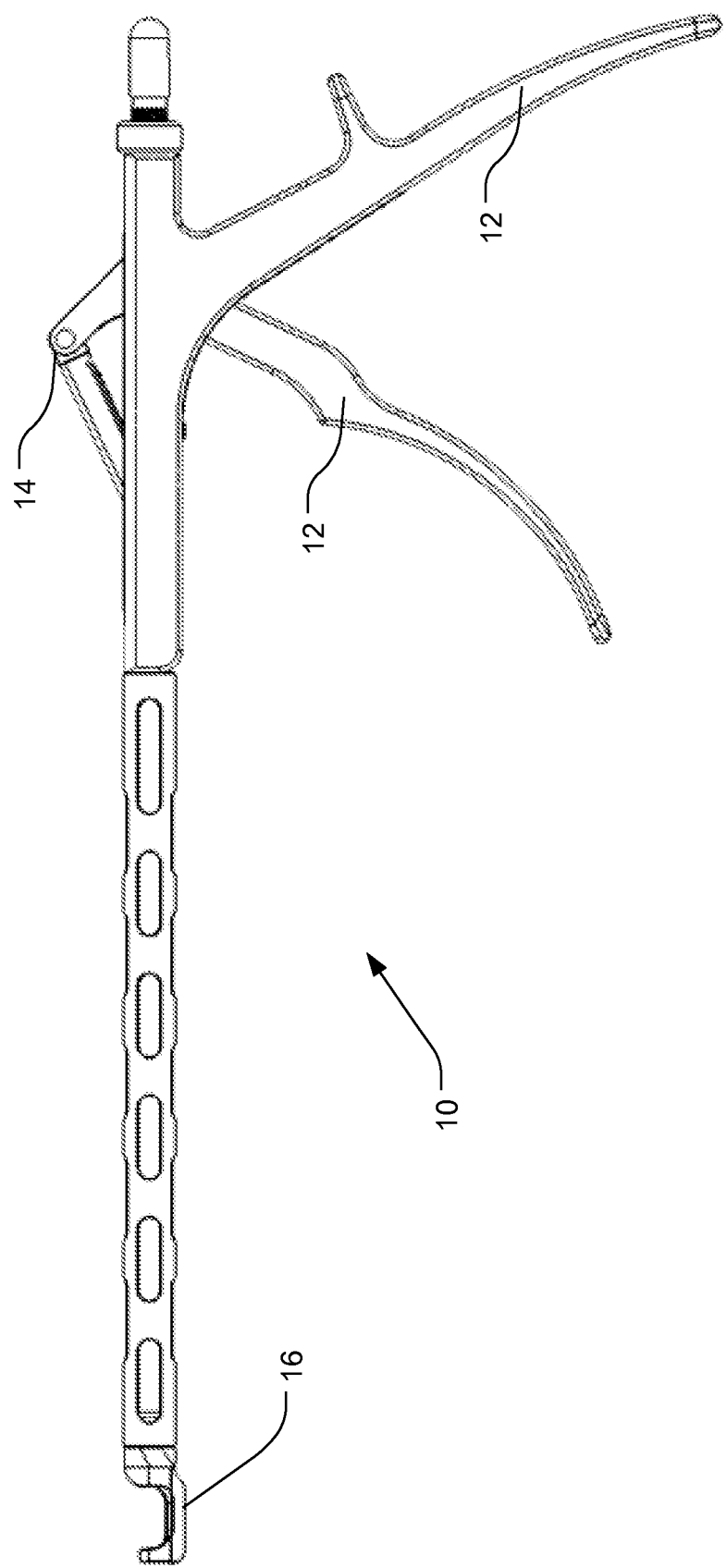
FIG. 1 shows a side view of a locker in an unactuated state.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

As used herein, the singular forms "a" and "the" can include plural referents unless the context clearly dictates otherwise. Thus, for example, reference to "a coupler" can include one or more of such couplers.

As used herein, the term "substantially" refers to the complete or nearly complete extent or degree of an action, characteristic, property, state, structure, item, or result. As an arbitrary example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. As another arbitrary example, a composition that is "substantially free of" an ingredient or element may still actually contain such item as long as there is no measurable effect thereof.

As used herein, the terms "attached," "coupled," "fixed," etc., can be used to describe a condition in which two or more components are coupled to one another in such a manner that they function as intended: that is, the force required to uncouple the components is sufficiently large such that the components will remain attached to one another during the service for which they were designed. Unless indicated to the contrary, such "coupled" components can be separable if sufficient force is applied to the components. In some aspects of the invention, components are elastically fixed or coupled to one another and will remain fixed during the useful life of the product for which they are designed; however, they may be uncoupled from one another using an appropriate level of force (applied in an appropriate manner and location), and will return to an original configuration (e.g., a condition, state, shape, size, etc.), which existed prior to the components being coupled to one another.

As used herein, when an area within a construct body is described as having a "decreased diameter," it is to be understood that the area described includes a diameter that is smaller than adjacent areas (either on one or both sides of the area of decreased diameter). For example, an area within a bore may have a decreased diameter as compared to other portions of the bore. In some embodiments, the area of decreased diameter within the bore will appear (although possibly not to the human eye) as an inner rib, or raised portion along the wall defining the bore, whereby that area of the bore has a smaller diameter than adjacent portions.

The term "body" can be used herein to refer to a variety of components of a surgical construct. For example, several components are illustrated in the Figures or in the applications incorporated herein by reference, including connecting rod(s), "T" coupler(s), end coupler(s), etc. Each of these components can be included within the scope of the meaning of the term "body." Additionally, a "body" may include two end couplers and the connecting rod extending therebetween.

As used herein, the term "interference fit" shall be interpreted broadly as including the joining of any two mating parts such that one or the other (or both) parts slightly deviate in size from their nominal dimension, thereby deforming such part slightly, each being compressed, the interface between two parts creating a union of extremely high friction. The word "interference" refers to the fact that one part slightly interferes with the space that the other is occupying in its nominal dimension.

In one aspect of the invention, an interference fit can be configured to require at least about 800 pounds of force to remove a male member from a female member. In one aspect of the invention, an interference fit can be configured to require at least about 600 pounds of force to remove a male member from a female member. In one aspect of the invention, an interference fit can be configured to require at least about 400 pounds of force to remove a male member from a female member. In one aspect of the invention, an interference fit can be configured to require at least about 200 pounds of force to remove a male member from a female member. In one aspect of the invention, an interference fit can be configured to require at least about 1200 pounds of force to remove a male member from a female member.

In some aspects of the invention, two members or components that are held together by an interference fit can be rigidly coupled to one another such that the components are immovable relative to one another, or are not freely moveable relative to one another. Such an interference fit can retain the components in position relative to one another during normal use or operation of the components. In most cases, an interference fit, as that term is used herein, will provide a coupling bond that results in components being immovably coupled to one another to such a degree that a typical human operator cannot manually decouple the components without the use of tools. In most cases, an interference fit, as that term is used herein, will provide a coupling bond that results in components being immovably coupled to one another to such a degree that they are essentially immovable relative to one another under normal physiologic loads of the spine.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The present invention relates generally to surgical construct systems, and systems and methods for installing such construct systems. Generally speaking, the surgical construct systems include one or more components that can be installed within anatomy of a patient, such as pedicle screws and the like. A construct can be configured to be coupled to the pedicle screw. The various inventive aspects of the technology are illustrated and explained in greater detail with reference to the attached figures and drawings.

In addition to the apparatuses provided, the present technology provides superior methods of installing such constructs, and coupling various components of the constructs one to another. In accordance with one aspect of the invention, a method of assembling a surgical construct is provided, including installing a fastener within a bone of a patient. Such a fastener can include, for example, a pedicle screw with a rounded or spherical head, or with a generally cylindrical head. A connector rod can be positioned on the fastener and an interference or press fit can be created between the fastener and the rod. In this manner, the two surgical components can be quickly and securely coupled one to another with very little effort required on the surgeon's part. In addition, much less trauma is experienced by the patient, in comparison to conventional attachment methods.

In one embodiment, the interference or press fit between the fastener and the rod is accomplished immediately after positioning the connector rod on the fastener. That is, no additional steps are necessary or desirable. Thus, for example, the surgeon can simply position the rod over the fastener, and very quickly and accurately couple the two one to another. A securing device can be used to couple the fastener and the rod, such as that shown by example in the figures/drawings. The securing device can engage the fastener and the rod, and can then push the rod over the fastener as the surgeon activates the gripping mechanism shown. Alternate securing devices may also be developed and used as appropriate or preferred.

In one aspect of the invention, a method of assembling a surgical construct is provided, consisting essentially of: installing a fastener within a bone of a patient; positioning a connector rod on the fastener; and creating an interference or press fit between the fastener and the rod.

In exemplary aspects of the invention, an interference fit, which may also be known as a compression fit, or a press fit, may be achieved through an act of causing translation of a surgical screw which is or comprises a male member, relative to a body having a female member or bore. As the outer surface of the male member of the pedicle screw is translated relative to and engages the inner surface of the bore or female member of the body of the surgical construct, the interference fit is created. As the forces necessary to create the interference fit exceed those that can generally conveniently be created by the unaided human, a securing device is commonly used by the surgeon to facilitate creation of the interference fit.

The PressON Spinal Fixation System is a modular assembly of rods (bodies) and screws. The simplest embodiment of the system includes a fixed length rod attached to pedicle screws, specifically two pedicle screws, at end couplers or tulip bodies. The rod may be straight or it may have a bend to it. Advantages of this embodiment include low bulk, high strength, low cost, and simple technique. The rod may be provided in various lengths at, for example, 1 mm increments. The screws may be provided at various lengths and diameters, for example, four diameters and various lengths with 5 mm increments. The system is polyaxial; the appropriate length rod can be attached to the pedicle screws at any relative angle between the rod and the screw that is within a 60 degree cone. Once attached, the system is rigidly locked.

The rod is locked to the screw by an elastic interference fit, press fit, or compression fit; the diameter of the screw head is larger than the opening in the rod by an amount that does not cause permanent deformation to either component when locked. The novel locking mechanism produces a stronger lock, is simple to deploy, and is inexpensive to manufacture. A locking instrument generates more than 5000 newtons of force to pull the screw into the coupler of the rod. The locking is no-torque such that no force need be transmitted to the spine. The system and design, however, also allows the application of desired forces to the spine to effect compression, and/or distraction, and/or reduction. For example, a short rod might be selected and the locking will simultaneously pull the pedicle screws toward each other to effect compression.

Unlocking is accomplished by pushing the screw out of the rod. Unlocking requires more than 5000 newtons of force. A threaded unlocker or a trigger-actuated unlocker produces the substantial mechanical advantage needed to generate the requisite unlocking force.

The modularity of the PressON Spinal Fixation System allows for options in selecting the components of the assembly. One might choose a rod that has preassembled set screws and screw balls. Such a rod would be mated with pedicle screws that do not have spherical heads, but that have generally cylindrical heads instead. The rod is delivered preassembled with the set screws and screw balls. The pedicle screw can be intra-operatively assembled to the rod. Snapping the rod assembly onto the pedicle screw requires only approximately 5 pounds of force, but pulling it off requires greater than 1200 pounds of force. The screw balls cannot flip upside down, but can receive the pedicle screw at any relative angle within a 60-degree cone. In the unlocked state, the system is poly-axial, and the screw balls have room to wiggle within the rod, which facilitates assembly in difficult cases.

Locking of the modular assembly is accomplished by driving the set screw to push the screw ball and pedicle screw into the elastic interference position; the diameter of the screw head is larger than the opening in the rod by an amount that interferes but that does not cause permanent deformation to either component. Advantages of the multi-component assembly include that the nested set screws cannot cross thread, and that the nested screw balls can wiggle within the rod to facilitate the subsequent, planned application of compression or distraction to the spine by the act of locking the assembly.

Figure 2:
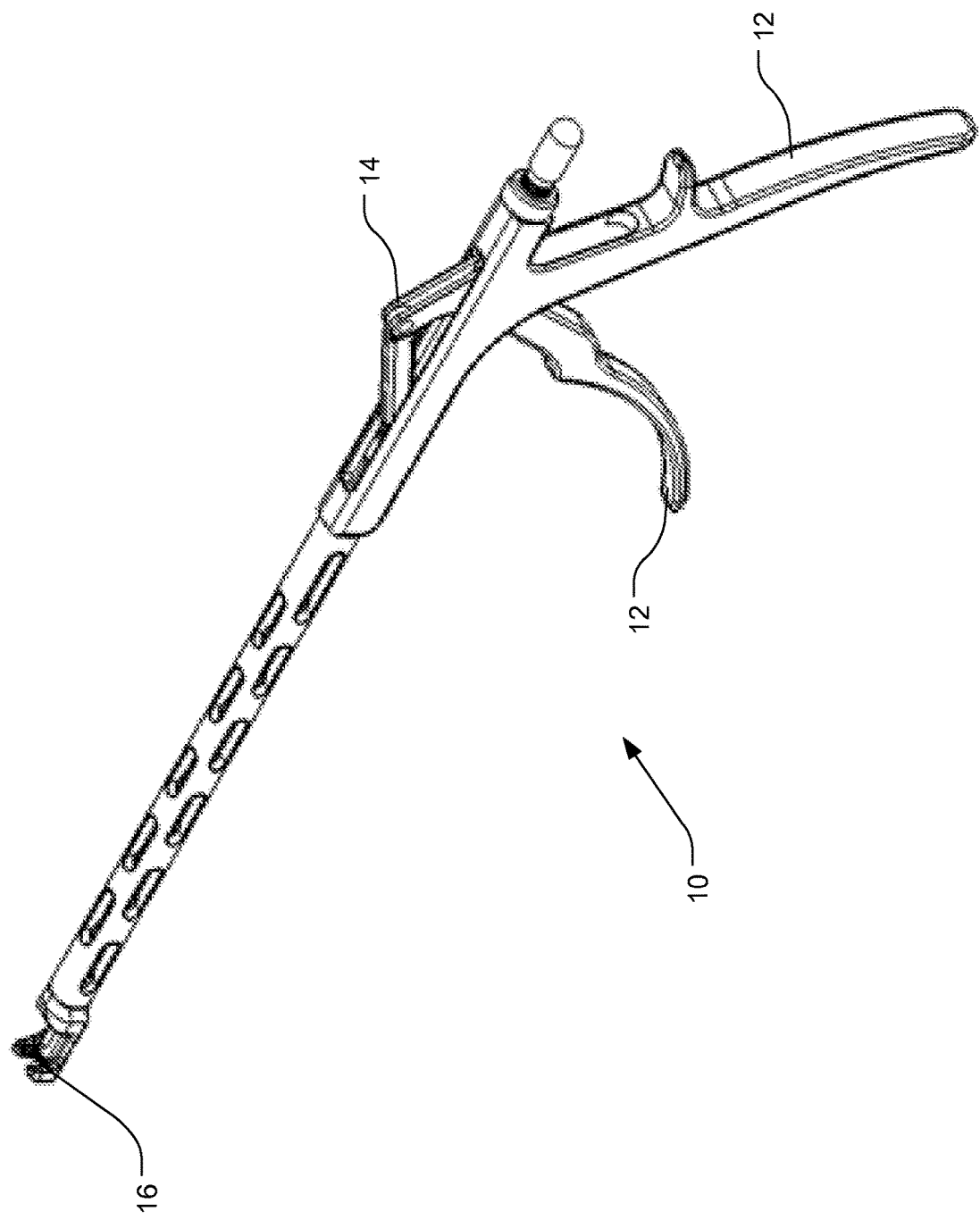
FIG. 2 shows a perspective view of the locker of FIG. 1.
Figure 3:
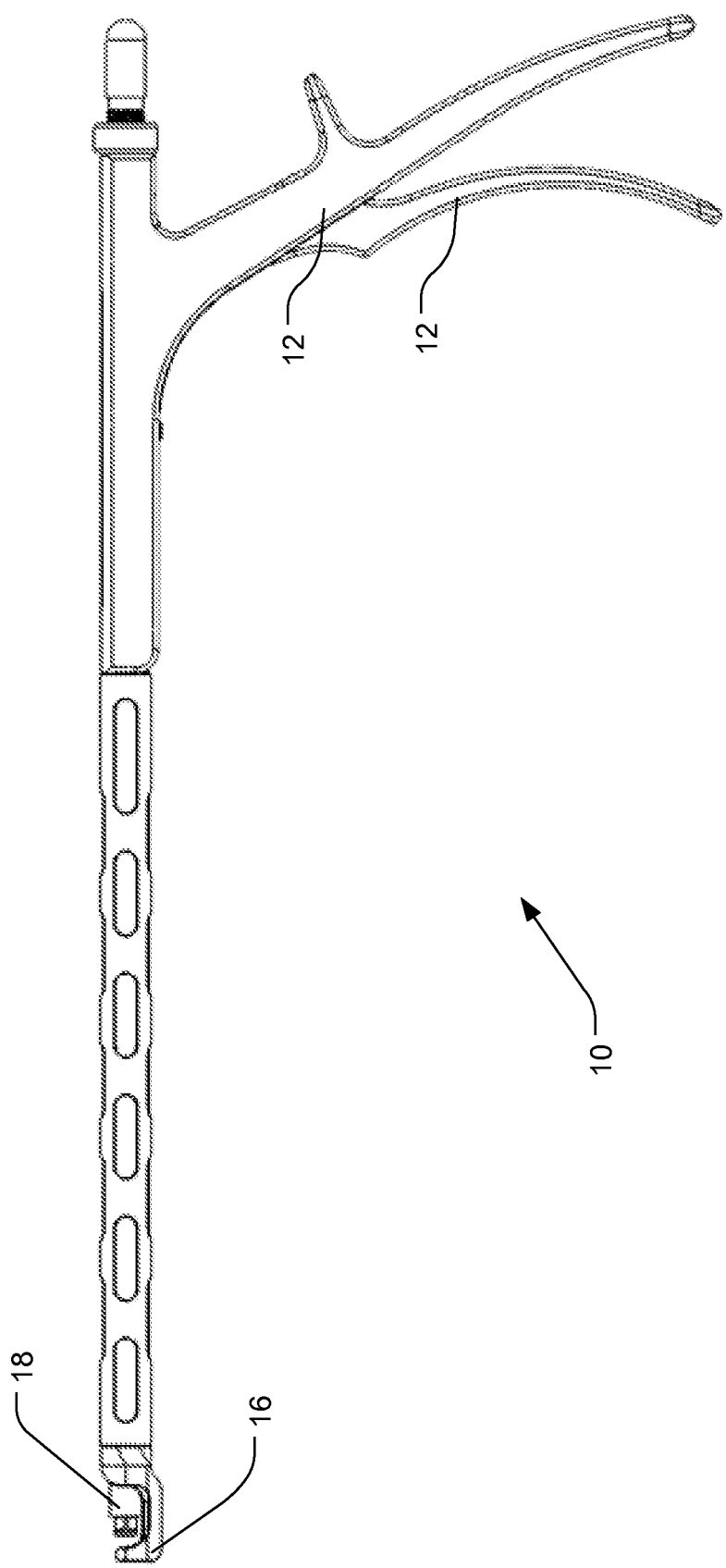
FIG. 3 shows a side view of the locker of FIG. 1 in an actuated state.
Figure 4:
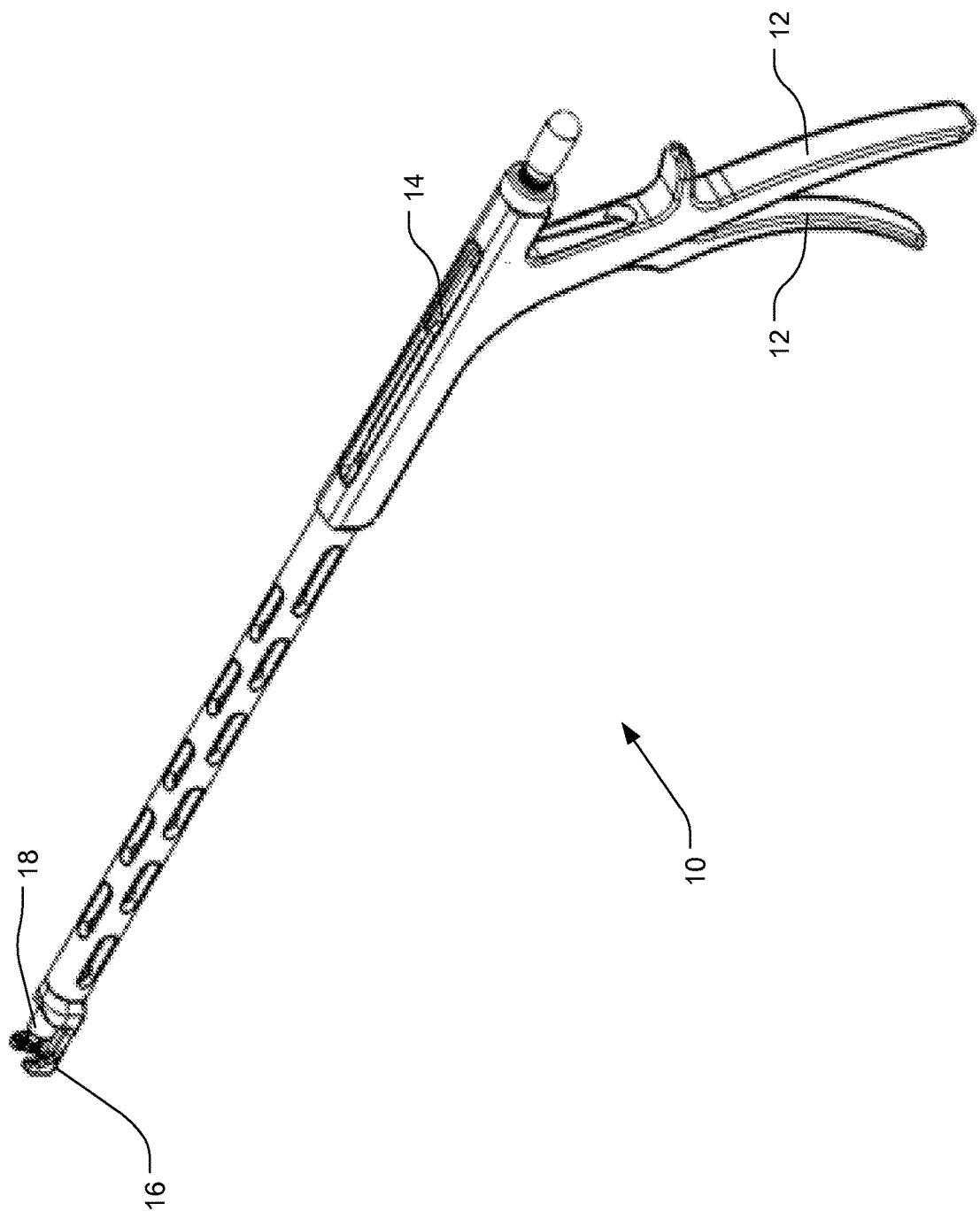
FIG. 4 shows a perspective view of the locker and state of FIG. 3.

FIGS. 1-4 shows one example of a securing device, a pistol-style locker 10. FIGS. 1 and 2 show side and perspective views, respectively, of the locker 10 in an unactuated or open position, while FIGS. 3 and 4 show side and perspective views, respectively, of the locker 10 in a fully actuated or closed position. The locker 10 includes handles 12 adapted to receive a hand or hands of a surgeon. When the handles are squeezed or triggered by the surgeon, the force created thereby is passed and multiplied through a linkage 14 and the increased force is delivered to elements of the locker 10 at a construct-engaging tip 16.

The linkage 14 may include any type of force-multiplying linkage appropriate for a desired multiplication of force, and may include, for example, a crank slider mechanism that advances an internal rod or ram rod (not shown in FIGS. 1-4) toward the construct-engaging tip 16 at the distal end of the instrument. As the handles 12 are fully engaged, with one handle 12 acting as a trigger, a rod tip 18 of the internal rod advances to a maximal extent toward the most distal portions of the locker 10, which are fixed, allowing a force to be delivered between the fixed distal portions of the locker 10 and the rod tip 18. The final distance between the rod tip 18 and the fixed distal portions of the locker 10 may be set by adjusting a calibration bolt during assembly or thereafter, such that the final fully-actuated position of the rod tip 18 can be set very precisely (such as within approximately 0.001-0.002 inches (approximately 0.025-0.05 mm) of a specified value) relative to the fixed distal portions of the locker 10. Such calibration of the instrument's closed position ensures a consistent fully actuated position, with a hard-stop and peak mechanical advantage occurring at an optimal point for locking a body of the surgical construct to a pedicle screw. While FIGS. 1-4 show embodiments of a locker 10 that utilize handles 12 to transmit and multiply a squeezing force of the surgeon to effectuate locking of the body to the pedicle screw, other embodiments may be used, including embodiments with a variety of different linkages, embodiments that utilize a screw force to effectuate locking of the body to the pedicle screw, and a variety of other embodiments to permit application of sufficient force to lock the body to the pedicle screw.

Returning to the illustrated embodiment, the end of the rod of the locker 10 may be provided with a retention feature or with retention features that allows retention of a body of a surgical construct thereon while the body is delivered to the surgical site. One example of a retention feature is illustrated in FIG. 5-9, which generally illustrate closer views of the area of the construct-engaging tip 16. As may be seen in FIG. 5, the construct-engaging tip 16 includes a screw-engaging tip 20, which is sized and shaped to define an open-sided aperture adapted to receive and engage a ball head or spherical head of a pedicle screw. The ball head or spherical head of the pedicle screw is commonly a truncated spherical shape, with a threaded portion of the pedicle screw extending therefrom at one end of the truncated spherical shape, and a tool-engaging feature at the other end of the truncated spherical shape. The spherical portions of the screw head allow the screw head to engage the body of the construct at a variety of angles and rotations, as will become more apparent from portions of the discussion below. The screw-engaging tip 16 is adapted to engage a portion of the ball head or spherical head proximate the threaded portion of the pedicle screw once the pedicle screw has been screwed into the bone to the desired final extent, and the screw-engaging tip 16 is fixedly attached to the non-moving portions of the locker 10 such that as the locker 10 is actuated, the rod and rod tip 18 move relative to the screw-engaging tip 20.

The retention feature may be located on the rod tip 18, and thus moves with the movement of the rod tip 18. One embodiment of the retention feature is illustrated in FIGS. 5-9, and this embodiment includes flexible segments 22 adapted to retain the body on the end of the rod tip 18. The body includes a receptacle adapted to receive the head of the pedicle screw therein while forming an interference fit, a press fit, or a compression fit in the manner discussed herein and in the applications incorporated herein by reference. The receptacle may be formed as a bore of the body, and the bore may be cylindrical or approximately cylindrical at least through an area of engagement with the screw head, and the bore of the body forms an opening through which the screw head is introduced to the bore after the pedicles screw has been screwed in to the patient's bone to the desired final extent. The portion of the body that engages with the screw head may at times be referred to or known in the art as a tulip assembly or tulip body, even though the tulip assembly may at times not be an assembly but a single unitary construct.

On a portion of the tulip assembly or tulip body opposite the opening of the bore that is adapted to receive the screw head, a second opening is provided. The second opening is of a second bore that passes into the tulip assembly or tulip body. The second or upper bore may or may not be a threaded bore, and has an axis generally parallel to the axis of the screw-head-receiving bore. The second or upper bore may have a diameter that is smaller than, larger than, or similar to the diameter of the screw-head-receiving bore, but will be generally illustrated herein as being smaller than the diameter of the screw-head-receiving bore. The second or upper bore communicates with the screw-head-receiving bore, such that an object may pass through the second or upper bore and may contact and/or transfer force to a screw head retained in the screw-head-receiving bore when the screw head is retained by the interference fit, the press fit, or the compression fit. The transfer of force through the second or upper bore may be used to disengage the screw head from the body, when such is desired, as will be described in more detail hereafter.

The second or upper bore need not be exactly aligned with the screw-head-receiving bore for such contact and/or transfer of force to occur, nor need the axis of the two bores be exactly aligned or even exactly parallel, although ensuring that the two bores are at least approximately parallel allows a maximum portion of the applied disengaging force to the screw head. In the illustrated embodiments, the two bores are generally aligned and have a shared or nearly coincident axis, but it should be understood that modifications differing from such alignment fall within the scope of the intended invention, as long as the two bores communicate in such a way as to permit the transfer of a disengaging force through the second or upper bore to the screw head retained in the screw-head-receiving bore. Similarly, while the screw-head-receiving bore and the second or upper bore are illustrated herein as having approximately circular symmetry (discounting any threaded aspects, if present), other configurations fall within the scope of the embodiments of the invention, especially other configurations of the second or upper bore, which may take any of a variety of shapes while still permitting the transfer of a disengaging force therethrough.

Figure 5:
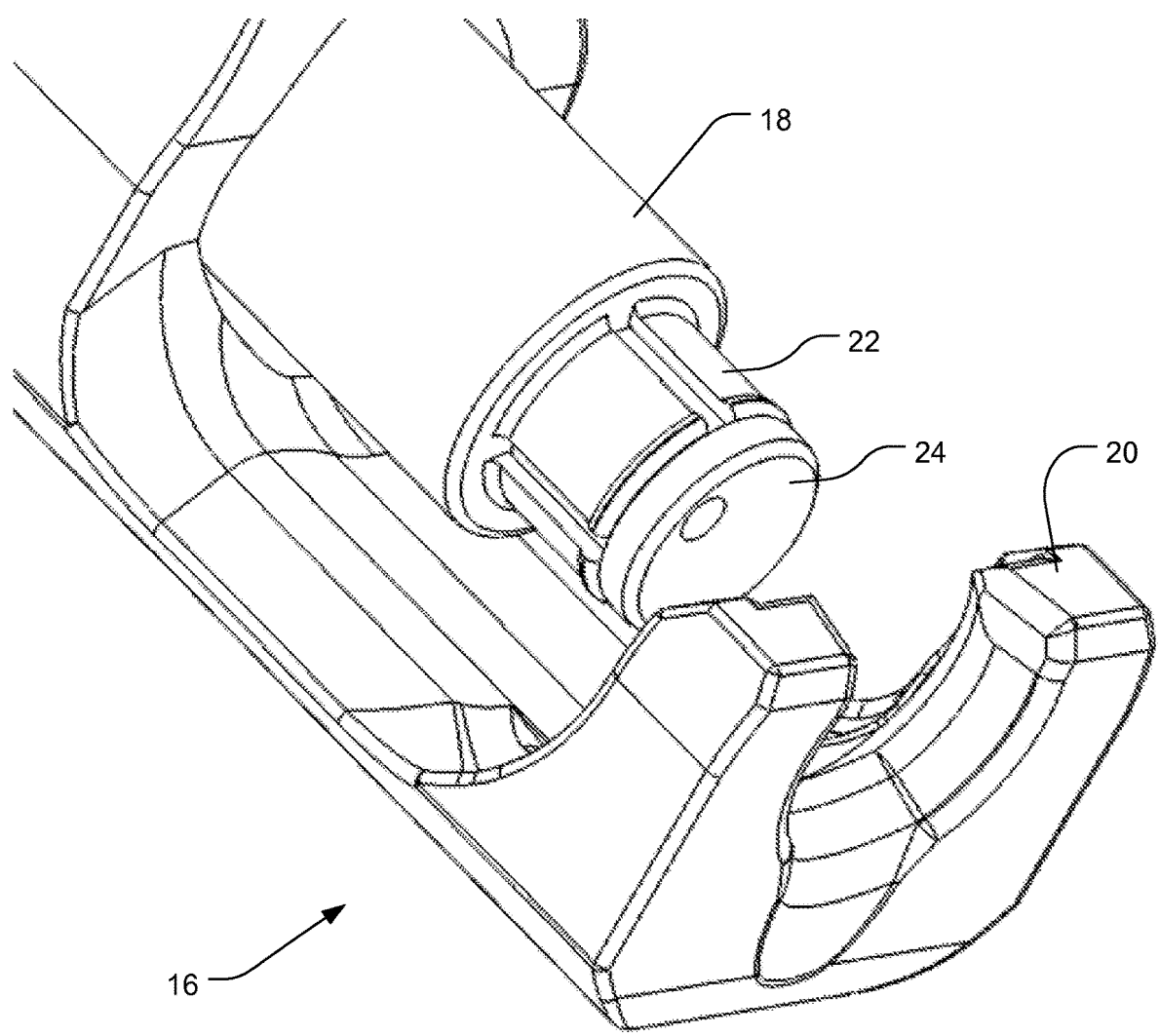
FIG. 5 shows a perspective view of a distal tip of the locker of FIG. 1.
Figure 6:
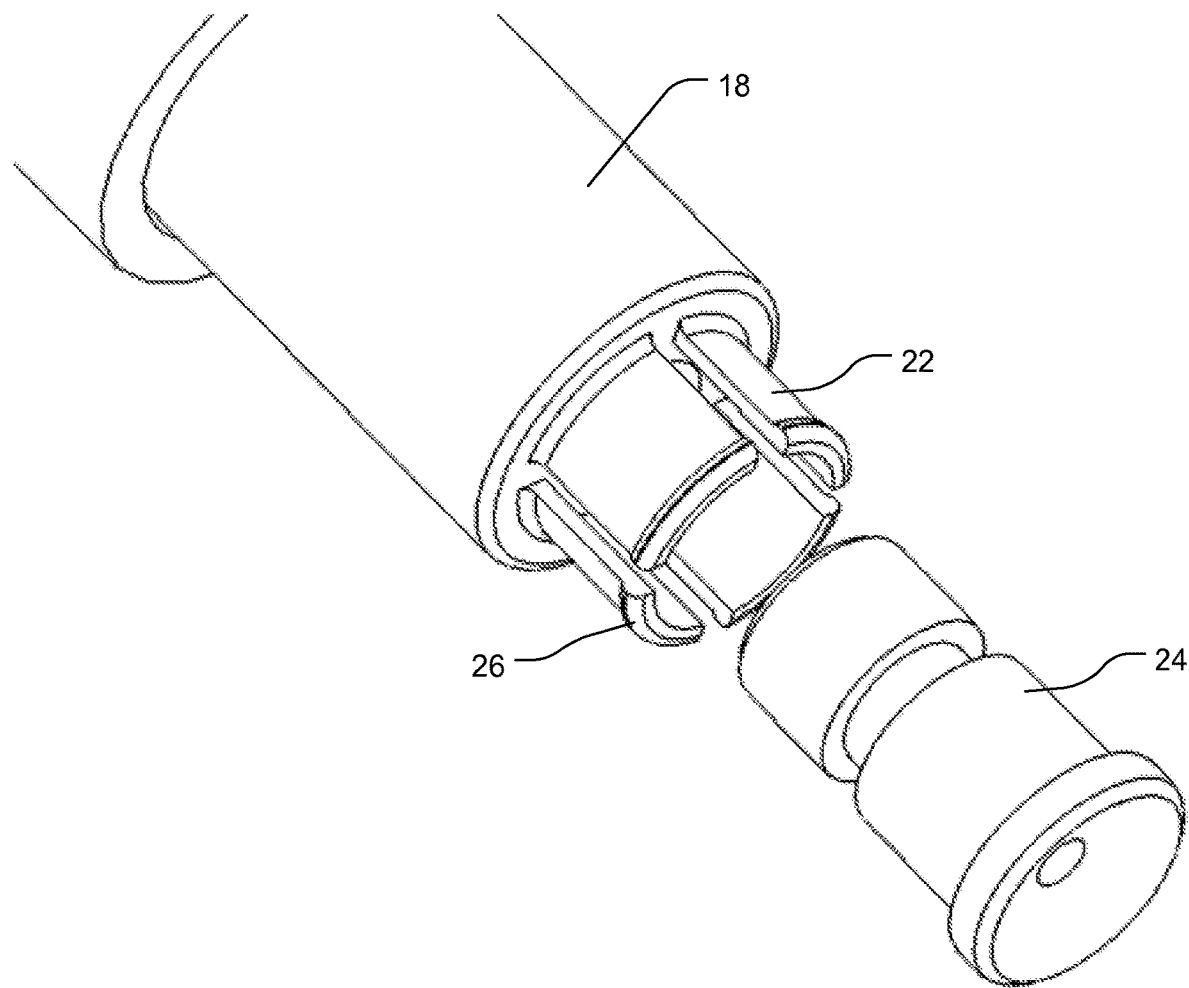
FIG. 6 shows an exploded view of a distal tip of a rod of the locker of FIG. 1.

The retaining feature of the locker 10 is adapted and configured to engage the second or upper bore of the tulip assembly or tulip body. As the illustrated and discussed embodiments of the second or upper bore of the tulip assembly or tulip body have an approximately circular symmetry, the illustrated embodiment of the retaining feature of the locker has an approximately circular symmetry as well. The corresponding shapes of the retaining feature and the second or upper bore allow the locker 10 to be used to deliver the body to the surgical site without the use of a separate body-holding instrument. Thus, as best illustrated in FIGS. 5 and 6, the flexible segments 22 may be arranged with circular symmetry on the distal end of the rod tip 18. FIG. 5 shows a perspective view of the construct-engaging tip 16 fully assembled, while FIG. 6 shows a perspective exploded view of the retaining feature (omitting the screw-engaging tip 20).

In their un-deflected position the flexible segments 22 have a larger outer diameter than the inner diameter of the opening at the top of the tulip assembly or tulip body, and of the corresponding second or upper bore. As the rod tip 18 is pushed into the second or upper bore (such as when the trigger on the locker 10 is actuated), the flexible segments 22 deflect inward as the rod tip 18 passes through the opening at the top of the tulip assembly or tulip body and into the second or upper bore. The plastic (permanent) deflection of the flexible segments 22 is prevented by a post 24 that is integrated into the rod tip 18. The flexible segments 22 come into contact with this rigid post 24 prior to plastically deforming, preventing damage in the case of poor alignment or user misuse.

The retention force (the force to insert or remove the retention feature into the second or upper bore) is such that the tulip assembly remains associated with the retention tip as the implant or implant body (e.g. a fixed-length rod terminating in tulip assemblies or tulip bodies, or an adjustable-length rod terminating in tulip assemblies or tulip bodies) is delivered to the surgical site, but not so much that the surgeon finds it difficult to remove the retention feature from the implant or implant body after locking the engaged tulip assembly or tulip body to the head of a pedicle screw. Thus, after the surgeon uses the locker 10 to lock the implant body to the head of the pedicle screw, the flexible segments 22 deflect again as the rod retracts, and the retention feature passes back through the top of the second or upper bore. The flexible segments 22 may be sized such that during the steps of retention and removal, the flexible segments 22 may deflect an amount appropriate to provide a desired retention force. By way of example only, the flexible segments 22 may be sized so as to deflect an amount in the range of approximately 0.001 inches (approximately 0.025 mm) to approximately 0.020 inches (approximately 0.5 mm).

Figure 7:
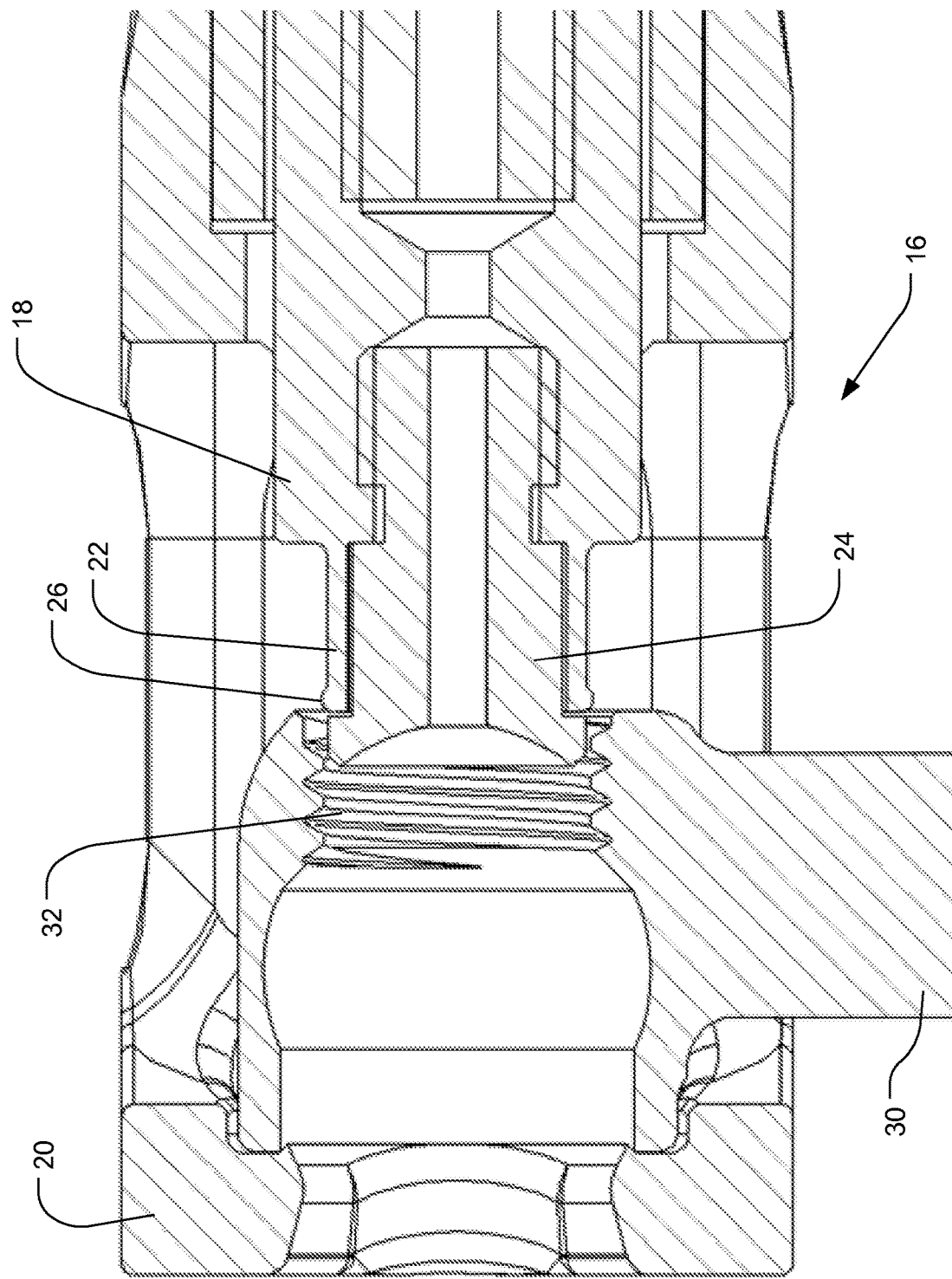
FIG. 7 shows a sectional view of a distal tip of the locker of FIG. 1 with a body provided therein prior to retention of the body on the distal tip of the rod.
Figure 8:
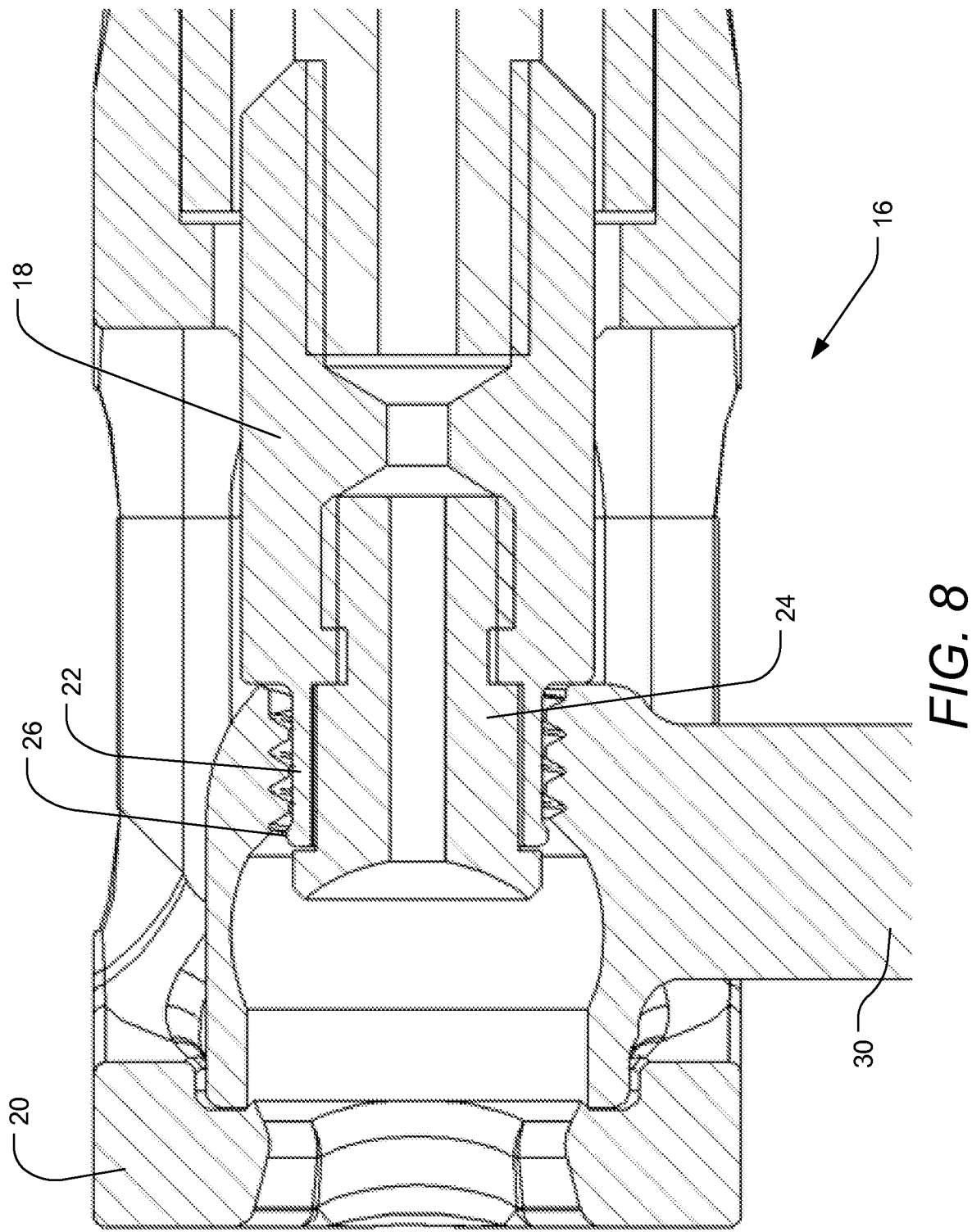
FIG. 8 shows a sectional view of a distal tip of the locker of FIG. 1 with a body provided therein upon retention of the body on the distal tip of the rod.
Figure 9:
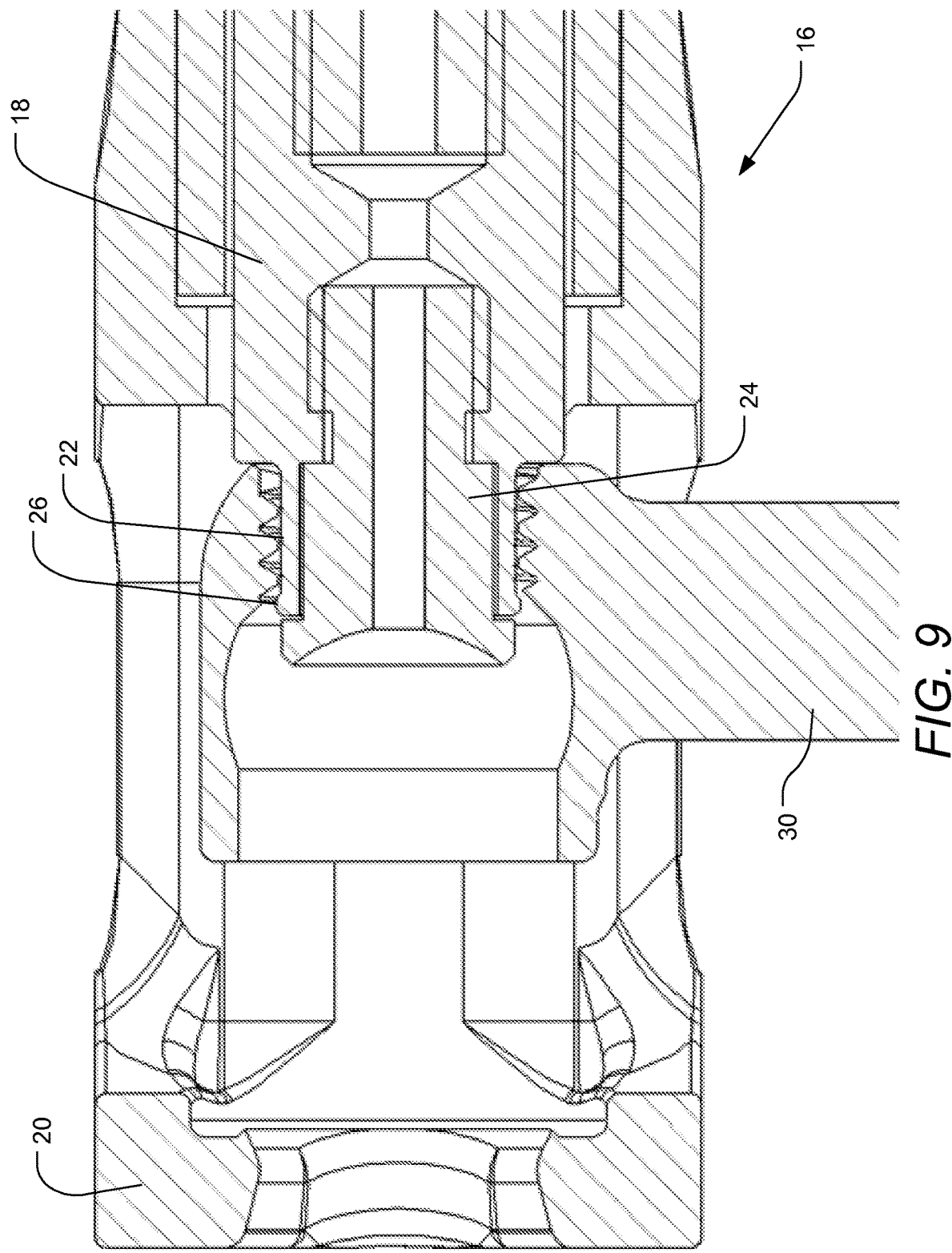
FIG. 9 shows a sectional view of a distal tip of the locker of FIG. 1 with a body provided therein subsequent to retention of the body on the distal tip of the rod and with the tip in position to accept a pedicle screw.

FIGS. 7-9 illustrate this process in cross-sectional or cutaway view. In FIG. 7, a body 30 is illustrated in cross section having been placed between the screw-engaging tip 20 and the rod tip 18. The screw-engaging tip 20 serves as a stop for the body 30 to secure the body 30 against movement while the locker 10 is engaged and operated to retain the body 30 on the rod tip 18. The surgeon may manipulate the body 30 until a second or upper bore 32 (which is threaded in the illustrated case) aligns with the rod tip 18, as shown in FIG. 7. The handles 12 of the locker 10 are further engaged, driving the rod tip 18 and the accompanying retention element into the upper bore 32 as shown in FIG. 8. The advancement of the rod tip 18 causes the flexible segments 22 to flex inward, being stopped from further inward movement by the post 24. Once the rod tip 18 is fully advanced into the second or upper bore 32 the retention features hold the body 30 on the rod tip 18, and the tension on the trigger or handles 12 can be released, whereby the rod tip 18 withdraws from the screw-engaging tip 20, drawing the body 30 with it, as shown in FIG. 9. In at least some embodiments, as illustrated in FIGS. 5-9, the flexible segments may be provided with one or more ridges 26 to further assist in securing the body 30 to the rod tip 18.

While FIGS. 5-9 illustrate one embodiment of a retention feature, other embodiments could retain body 30 to rod tip 18, which include but are not limited to a spring loaded element (such as a ball plunger), a retention feature consisting of or coated in a visco-elastic material which provides a reversible interference fit with the second or upper bore 32, a retention feature consisting of or having flexible segments 22 consisting of a super-elastic material which provides a reversible interference fit with the second or upper bore 32, or a retention feature consisting of a tapered post which has a self-holding profile (for example Morse taper, or Brown and Sharpe taper). Thus, the exemplary embodiment of FIGS. 5-9 should not be taken as limiting.

With the body 30 retained on the rod tip 18 of the locker 10, the body 30 is prepared to be introduced to the surgical site to be secured to the head of the pedicle screw. The distal end of the locker 10 is introduced to the surgical site, and the screw-engaging tip 20 at the distal end of the pistol locker is placed under the head of the pedicle screw which was previously inserted into the bone by the surgeon (in the illustrations of FIGS. 10-11, 15-17, 22-25, the bone is represented by a rectangular block/surface for simplicity of illustration). When using an embodiment where the head of the pedicle screw is spherical (in reality a truncated spherical shape), actuating the locker 10 advances the rod to press the body 30 onto the pedicle screw head, as shown in FIGS. 10 and 11.

Figure 10:
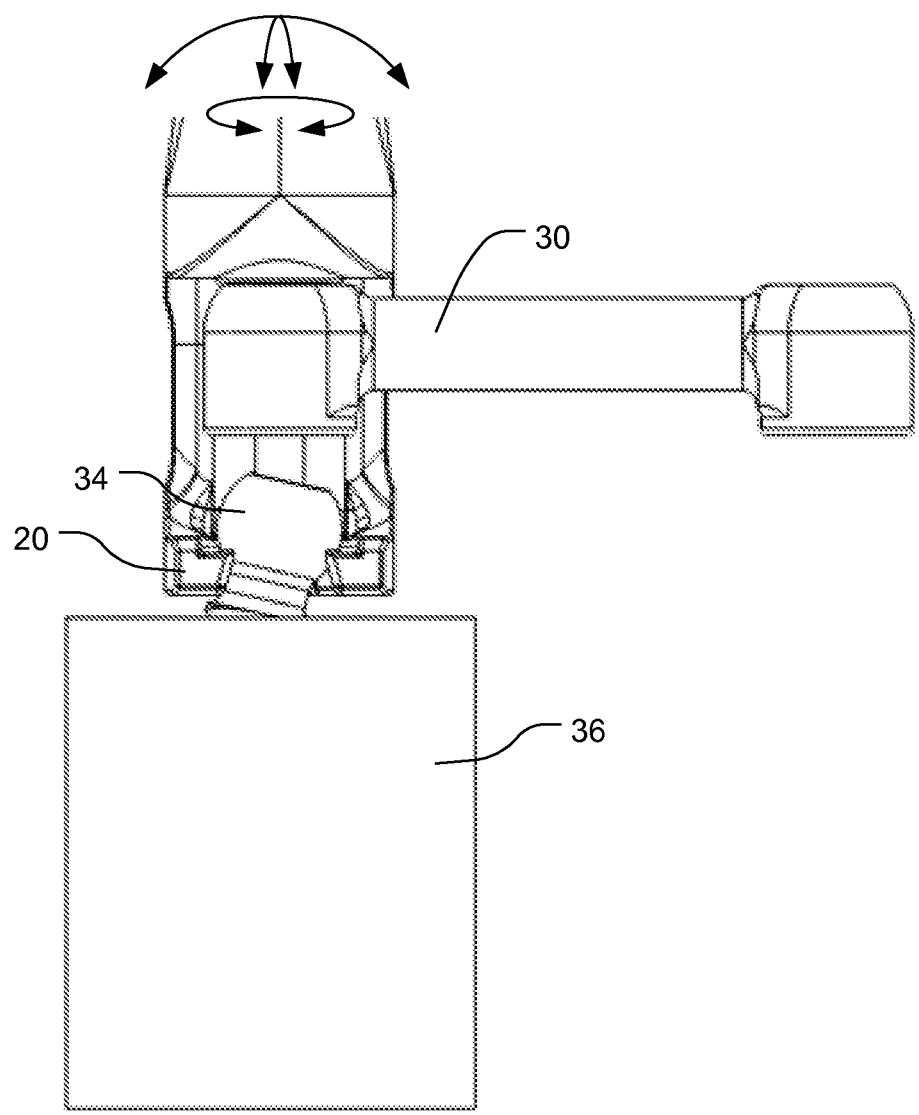
FIG. 10 shows a perspective view of the rod-body assembly prior to coupling of the rod to a pedicle screw.
Figure 11:
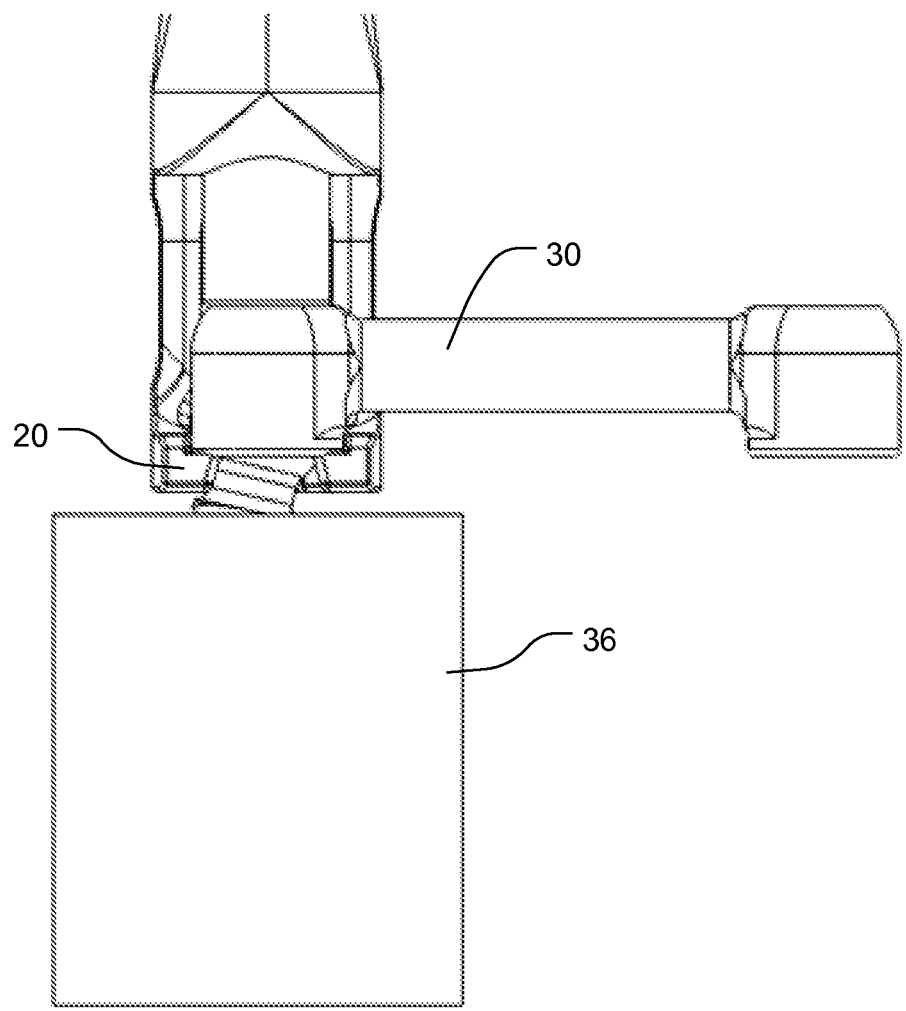
FIG. 11 shows a perspective view of the rod-body assembly upon coupling of the rod to the pedicle screw.

FIG. 10 shows the situation as the distal end of the locker 10 has been delivered to the surgical site, and the screw-engaging tip 20 has been located below the head 34 of a pedicle screw which has previously been screwed into a bone 36. As may be seen from FIG. 10, the truncated-spherical shape of the head 34 allows the locker 10 and body 30 to be oriented at a variety of angles and rotations (as represented by the arrows in FIG. 10) within a cone of approximately 30 to approximately 60 degrees before the body 30 is locked to the head 34 of the pedicle screw. Once the desired orientation has been achieved, the surgeon maintains the locker 10 in the desired orientation while actuating the handles 12 (i.e. pressing the trigger) of the locker 10, causing the rod to advance and the rod tip 18 and retained body 30 advancing toward to the screw head 34. Upon full actuation of the handles 12, the body 30 is forced on to the screw head 34, causing the body 30 to be coupled to the head 34 with an interference fit, press fit, or compression fit, as illustrated in FIG. 11. The surgeon then reverses the actuation of the handles 12, and the retention feature releases from the second or upper bore 32 (the flexible segments 22 of the illustrated embodiment are deflected as they are withdrawn from the second or upper bore 32), and the surgeon may remove the locker 10 by sliding the screw-engaging tip 20 from below the now-coupled head 34 and body 30.

Figure 12:
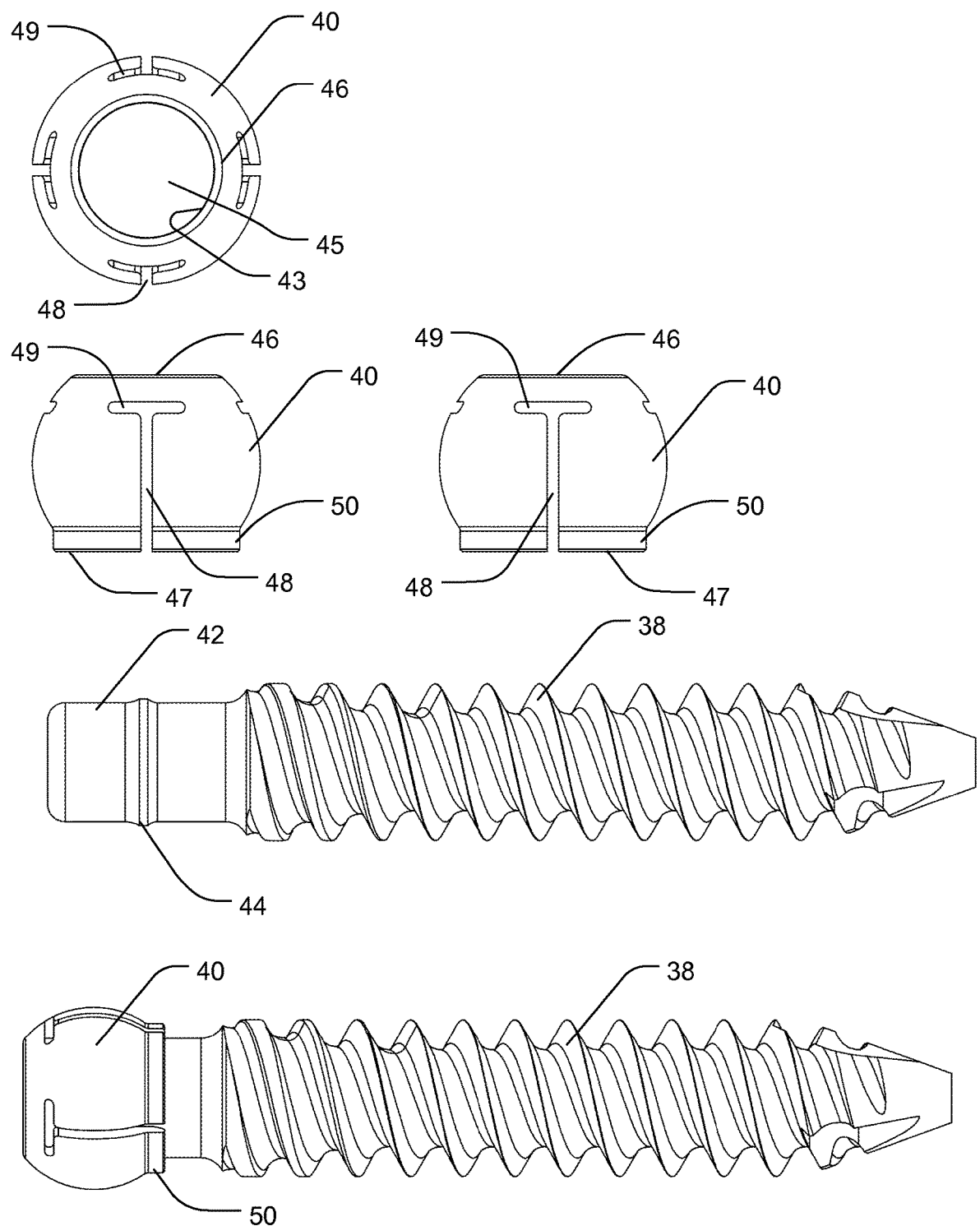
FIG. 12 shows multiple views of a screw ball, a pedicle screw having a generally cylindrical head, and a pedicle ball-screw assembly.

In an alternate embodiment, a pedicle screw does not have a truncated spherical head 34. Instead, the pedicle screw has a cylindrical head with a feature that allows the cylindrical head to lock to a screw ball. An example of such a pedicle screw (a "cylindrical pedicle screw 38") and of a screw ball 40) are shown in FIG. 12. As mentioned, the exemplary cylindrical pedicle screw 38 has a generally cylindrical head 42. The feature that allows the cylindrical head 42 to lock to the screw ball 40 may comprise any of a variety of features, such as one or more ridges 44 on the cylindrical surface of the screw head 42 or one or more channels on the cylindrical surface of the screw head 42. The screw ball 40 has a corresponding inner cylindrical surface 43 configured to engage the cylindrical surface of the screw head 42, and has corresponding features to engage the features of the screw head 42: if the screw head 42 has one or more ridges 44 on its surface, the screw ball 40 has one or more corresponding channels on its inner cylindrical surface 43, and if the screw head 42 has one or more channels on its surface, the screw ball 40 has one or more corresponding ridges on its inner cylindrical surface 43.

When the screw ball 40 is assembled to the cylindrical head 42 of the pedicle screw, the combined assembly (see bottom of FIG. 12) has a shape similar to the pedicle screw discussed above, with a spherical head (or truncated spherical head). As shown in FIG. 12, the screw ball 40 of such an embodiment thus has a generally truncated spherical shape, and the spherical shape is truncated where a generally cylindrical channel 45 passes through the screw ball 40. Therefore, the screw ball has a generally circular upper edge 46 and a generally circular lower edge 47, with the edges 46, 47 generally defined by the meeting of the generally spherical outer surface of the screw ball with the generally cylindrical inner surface 43 of the generally cylindrical channel 45 through the screw ball 40. To permit or facilitate assembly of the screw ball 40 to the cylindrical head 42 of the cylindrical pedicle screw 38, the screw ball 40 may be formed with generally vertical channels 48 extending from one or more of the upper edge 46 and the lower edge 47 around the screw ball 40. The vertical channels may optionally terminate in horizontal channels 49 as shown. Such channels 48, 49 allow the screw ball 40 to elastically expand as the generally cylindrical screw head 42 is inserted into the generally cylindrical channel 45 of the screw ball 40, and especially until the ridge(s) (e.g. ridge 44) of the screw head 42 or inner surface 43 engage their corresponding channel(s) (or until such other lock feature(s) as are present engage).

In certain embodiments where a pedicle screw with generally cylindrical screw head ("cylindrical pedicle screw 38") and a screw ball 40 are used, the body 30 of the construct may be delivered and assembled to the cylindrical pedicle screw 38 in a slightly different fashion than that discussed above. In such an embodiment, the screw ball 40 may be delivered to an inner portion of the screw-engaging bore that is slightly larger than the portion immediately adjacent the screw-receiving opening. The inner portion of the screw-engaging bore may have a generally cylindrical shape or a generally spherical shape, or it may have any other shape that accommodates and generally localizes the screw ball 40 or the screw ball and cylindrical pedicle screw assembly while allowing rotation and pivoting therein. The portion of the bore immediately adjacent the screw-engaging opening is the portion adapted to provide the interference fit, press fit, or compression fit, while the inner portion has a larger diameter and/or shape that allows the screw ball and/or assembled screw ball-pedicle screw construct to rotate and pivot more freely. The screw ball 40 is delivered to the inner portion before being assembled to the screw head 42, and any channels in the screw ball 40 may allow the screw ball 40 to compress to relatively easily pass the portion of the screw-engaging bore that is immediately adjacent the screw-engaging opening.

Once the screw ball 40 is within the inner portion of the bore, the head 42 of the cylindrical pedicle screw 38 may be introduced into the screw-engaging bore until it is introduced into the screw ball 40 and advanced to the point where the corresponding features of the screw ball 40 and the cylindrical pedicle screw 38 lock the screw ball 40 to the head 42 of the cylindrical pedicle screw 38. At this point, the screw 38 cannot be removed from the bore without first forming the interference fit, press fit, or compression fit at the location of the screw-engaging bore proximate the screw-engaging opening. The assembly of the screw head 42 to the screw ball 40 contained within the larger area of the screw-engaging bore generally occurs once the screw 38 has already been screwed into the patient's bone.

To prevent the screw ball 40 from rotating within the larger area of the screw-engaging bore to a position in which the screw ball 40 itself could block or prevent entry of the generally cylindrical head 42 into the screw ball 40, the generally cylindrical outer surface of the screw ball 40 may be modified in shape as shown in FIG. 12 to form an anti-flip lip 50 along the lower edge 47 of the screw ball 40 (the edge that first receives the head 42 of the cylindrical pedicle screw 38). Then, when the screw ball 40 is within the larger area of the screw-engaging bore, the anti-flip lip 50 prevents rotation of the screw ball 40 to a degree that would prevent entry of the generally cylindrical screw head 42 into the generally cylindrical channel 45 through the screw ball 40.

A potential advantage of the generally cylindrical screw head and screw ball combination is that the surgeon may place the body on both screw heads, and still manipulate the associated vertebra to some degree to achieve a desired alignment before finally locking the surgical construct by applying a force between the screw head and the body at each pedicle screw.

Figure 13:
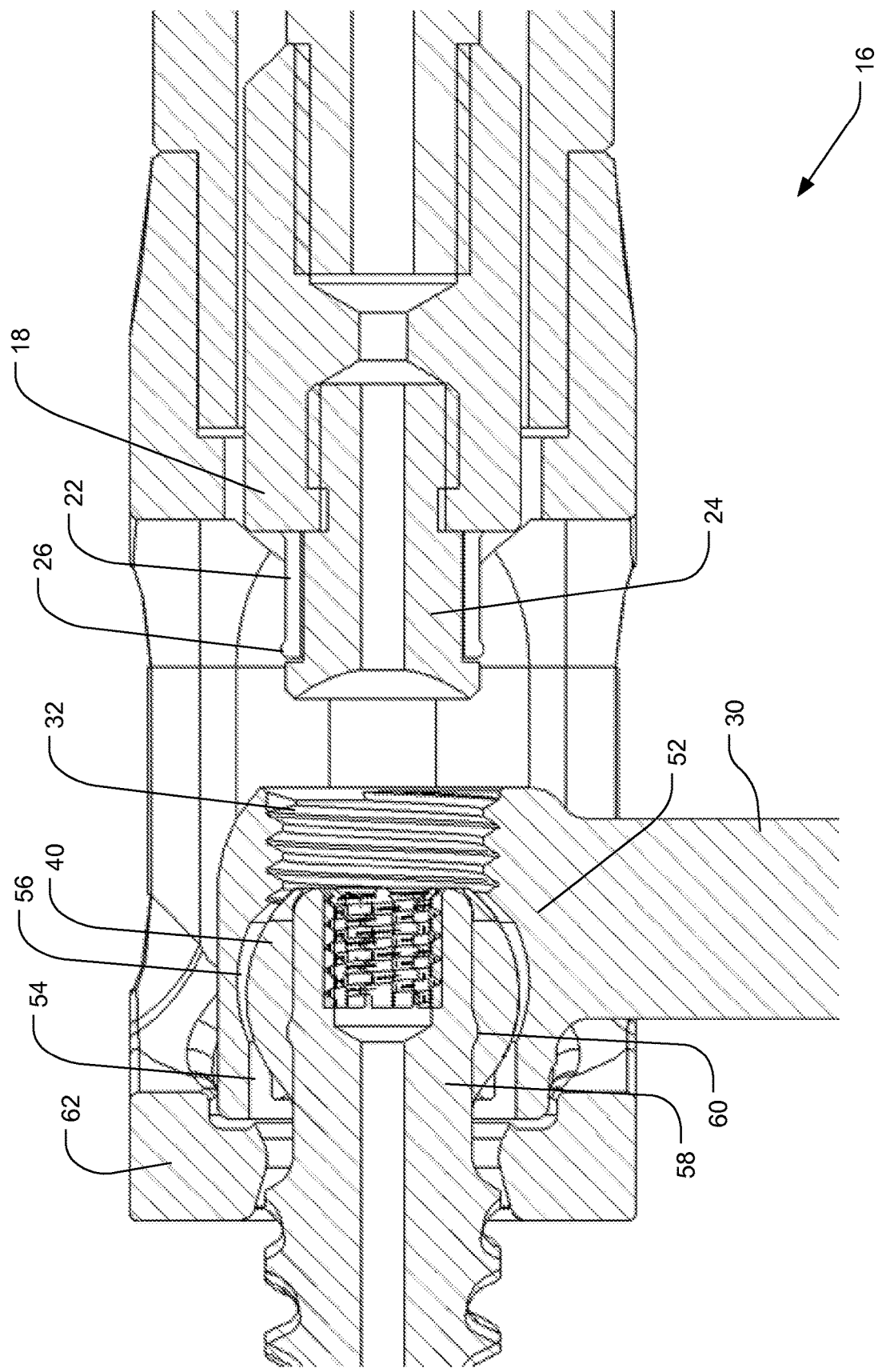
FIG. 13 shows a sectional view of a distal tip of a locker with a body-screw ball-pedicle screw assembly prior to interference coupling of the various components by the locker.
Figure 14:
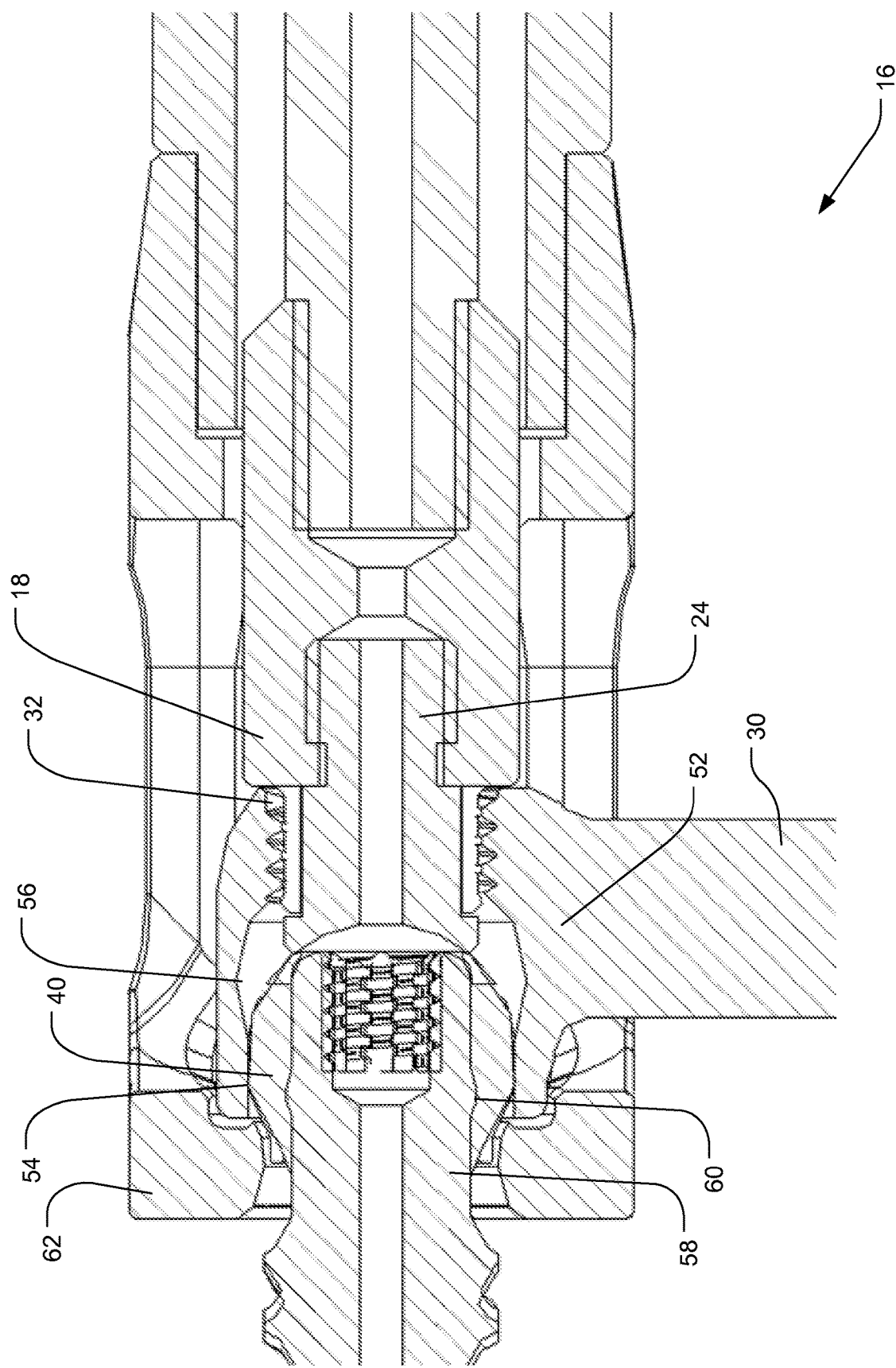
FIG. 14 shows a sectional view of a distal tip of a locker with a body-screw ball-pedicle screw assembly subsequent to interference coupling of the various components by the locker.

FIGS. 13-14 illustrate an exemplary method of locking of one example of a cylindrical pedicle screw and screw head embodiment. In this embodiment, the body 30 is assembled to a screw ball 40 by placing the screw ball 40 within the screw-engaging bore of a tulip assembly or tulip body 52, and by forcing the screw ball 40 past an interference fit area 54 of the bore into a larger inner portion 56 of the bore, where the screw ball 40 can move more freely. Meanwhile, at the surgical site, the cylindrical pedicle screw is screwed into the bone a desired amount. The body 30 (containing the screw ball 40) is introduced to the surgical site and snapped onto a generally cylindrical head 58 of the cylindrical pedicle screw until the head-ball locking feature(s) 60 fully engage, thereby producing an assembled but unlocked configuration of the pedicle-screw-body surgical construct. This configuration is illustrated in sectional or cutaway view in FIG. 13.

A modified version of a locking tool may then be used to lock the body 30 to the pedicle screw by forcing the cylindrical pedicle screw-screw ball assembly partially out of the bore until the portion of maximal diameter of the pedicle-screw-screw-ball assembly is within the interference fit area 54. The locking tool may be largely similar to the locker 10 discussed above, although it may have a different extent or location of maximal displacement of the rod tip 18, and the screw-engaging tip 20 may be modified to instead be a body-engaging tip 62 as shown in FIG. 13. Thus, after assembling the body 30 and screw ball 40 to the cylindrical head 58, the surgeon places the locking tool's body-engaging tip 62 (which still has an open side to permit passage of the screw body therethrough) under the tulip assembly or tulip body 52 and actuates the instrument to advance the rod to push the cylindrical pedicle screw-screw ball subassembly from the assembled-unlocked position (FIG. 13) into the locked state (FIG. 14).

With either pedicle screw embodiment, there is an interference fit, press fit, or compression fit established between the inner diameter of the bore of the tulip body 52/body 30 (which is smaller) and the spherical pedicle screw head 34 or screw ball 40 (which is larger). This interference fit requires a pressing force of approximately 800-1200 pounds and creates a rigid coupling between the body 30 and pedicle screw. The locker's or other locking instrument's actuating mechanism provides the mechanical advantage necessary for the surgeon to manually generate this large force. The non-moving elements of the locker 10 or other locking tool (such as the outer tube, the screw-engaging tip 20 or body-engaging tip 62 at the distal end which supports the pedicle screw or body) provide the structural rigidity to support the pressing force.

When the construct is locked with the locker 10 or other locking tool/instrument, the pedicle screw's axis may lie at an angle with respect to the axis of the body 30 or tulip body 52 as shown in several of the Figures. This angulation may occur in one or two planes. Thus, the possible orientations of the pedicle screw with respect to the body 30/tulip body 52 lie within a conical region whose vertex is at the center of the pedicle screw's head. The included angle of this conical region is commonly referred to as the poly-axial angle, and can range from approximately 30 to approximately 60 degrees.

Using the locker 10 or other locking tool/instrument to generate an interference fit between the pedicle screw head 34 or cylindrical pedicle screw-screw ball assembly and the body 30 eliminates the need for instruments found in many existing pedicle screw and rod systems. Instruments that are not needed include a rod holder (as discussed above) and a counter torque (counter torques are required when assembling pedicle screws which use set screws to lock the rod to the pedicle screw—with the locker 10 and similar devices, no torque is applied to the pedicle screw during locking, there is no need for a separate counter torque instrument). Additionally, when using the locker 10 and similar tools/instruments there is no possibility of cross threading or other misalignment between the construct components. Cross threading of the set screw found in many existing pedicle screw systems is a common issue raised by surgeons who use such systems.

In one embodiment of the locker 10, the actuating mechanism is a four-bar, change-point, crank slider mechanism with a total travel of approximately 0.539 inches (approximately 13.7 mm) between its fully open (unactuated) and closed (actuated) positions. However other means of achieving high mechanical advantage may alternatively be used, which may include, but are not limited to, other high-mechanical advantage mechanism linkages (four-bar, five-bar six-bar, etc), replacing the ram rod with a threaded rod (turn the threaded rod to advance the rod tip 18 with significant mechanical advantage), and hydraulic or pneumatic pistons.

The amount of force and travel generated by the actuating mechanism of the locker 10 or similar locking tools/instruments may be varied to suit a particular embodiment or use of the PressON Spinal Fixation system as discussed herein and in the applications incorporated by reference. For example, if the force required to generate the interference fit were increased, the actuating mechanism and structural elements could be adjusted to generate and support the increased load. Similarly, for example, if it were found to be desirable to have increased clearance between the body 30 and the pedicle screw head 34 prior to locking, the actuating mechanism and structural elements could be adjusted to give greater ram rod travel.

Figure 15:
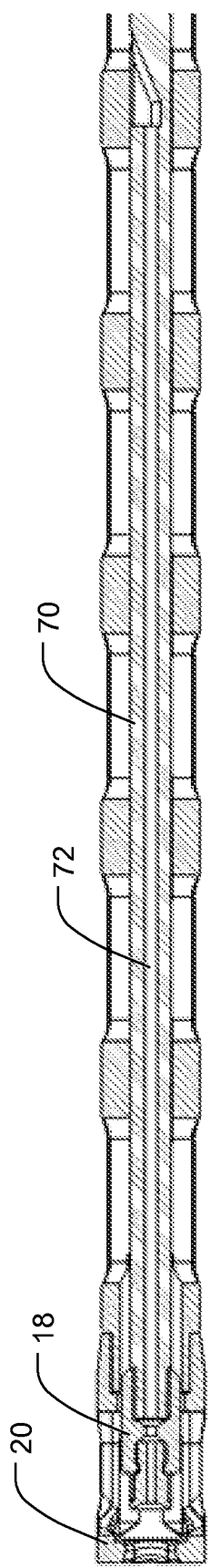
FIG. 15 shows a sectional view of an embodiment of a body of a locker having a cannulated rod therethrough.

In one embodiment, as illustrated in FIG. 15, a ram rod 70 of the actuating mechanism may be cannulated (have an internal channel 70 with exit point) to allow the locker to pass over a guide wire. Alternately, the full instrument may be cannulated (a path for the guide wire passes through the entire instrument). When using a guide wire, the pedicle screw is first placed over the guide wire and then driven in to the bone. Then, the locker or similar instrument or tool is fed over the guide wire so that the surgeon can guide it to the pedicle screw head 34 without being able to visualize the pedicle screw head 34. The guide wire could then be removed immediately prior to or immediately after locking.

Thus, the instruments needed for a typical, status quo pedicle screw system are significantly greater in number and complexity than the instruments required when using the locker 10 or other similar devices with the PressON Spinal Fixation System as discussed herein and in the applications incorporated herein by reference. The list below assumes the surgeon has prepared the pedicle pilot hole with their preferred instrumentation (drill, burr, awl, probe, tap, etc.).

The instruments used with typical pedicle screw system for a single level construct (listed in order of use) are: 1) a screw retaining sleeve—assemble to pedicle screw; 2) a pedicle screw driver, 3) a screw retaining sleeve—disassemble from pedicle screw, 4) a tulip placer—snap on tulip for systems that allow the tulip to be introduced after the screws are inserted, 5) a head turner—orient tulips to receive rod, and 6) a rod holder—may be used more than once while finding correct rod length. To fully lock the first screw, and partially lock the second screw, the following instruments are used: 7) a counter torque, 8) a locking cap driver, and 9) a torque limiting t-handle. Then, the following tools are used to complete alignment of the construct: 10) a compressor/distractor and 11) a persuader—if necessary, not common on one level constructs. To fully lock the second screw, the following instruments are used: 12) a counter torque, 13) a locking cap driver, and 14) a torque limiting t-handle.

In contrast, the instruments used with typical PressON Spinal Fixation System for a single level construct (listed in order of use) are: 1) a pedicle screw retaining driver, 2) a caliper—to measure the inter-pedicular screw distance (screw head-center to screw head-center), and 3) the locker 10 or other similar instrument. Therefore, advantages of the system include a great reduction in the complexity of the surgical procedure and a concomitant reduction in the number and complexity of surgical tools needed, with accompanying reductions in cost.

Another advantage of the system is that the position of spinal segments can be manipulated through the appropriate selection of length of the body 30 (e.g. of a rod connecting adjacent tulip bodies 52 or tulip assemblies) and the use of the locker 10 or similar tools (in the discussion hereafter, references to the locker 10 should be understood to refer to the locker 10 and to variations thereof such as have been discussed herein). In each case it is assumed that the surgeon has appropriately released the surrounding soft tissues to allow mobilization of the spinal segment.

Manipulation of the body 30 at the surgical site is made possible because of the retention feature on the rod tip 18. This retention feature allows the surgeon to manipulate the locker 10 to apply forces to the body, allowing the surgeon to adjust the body's orientation prior to locking. Selection of the length of the body and manipulation of the body's orientation prior to locking allow the surgeon to achieve compression of the intervertebral space, distraction of the intervertebral space, and/or reduction of spondylolisthesis.

Figure 16:
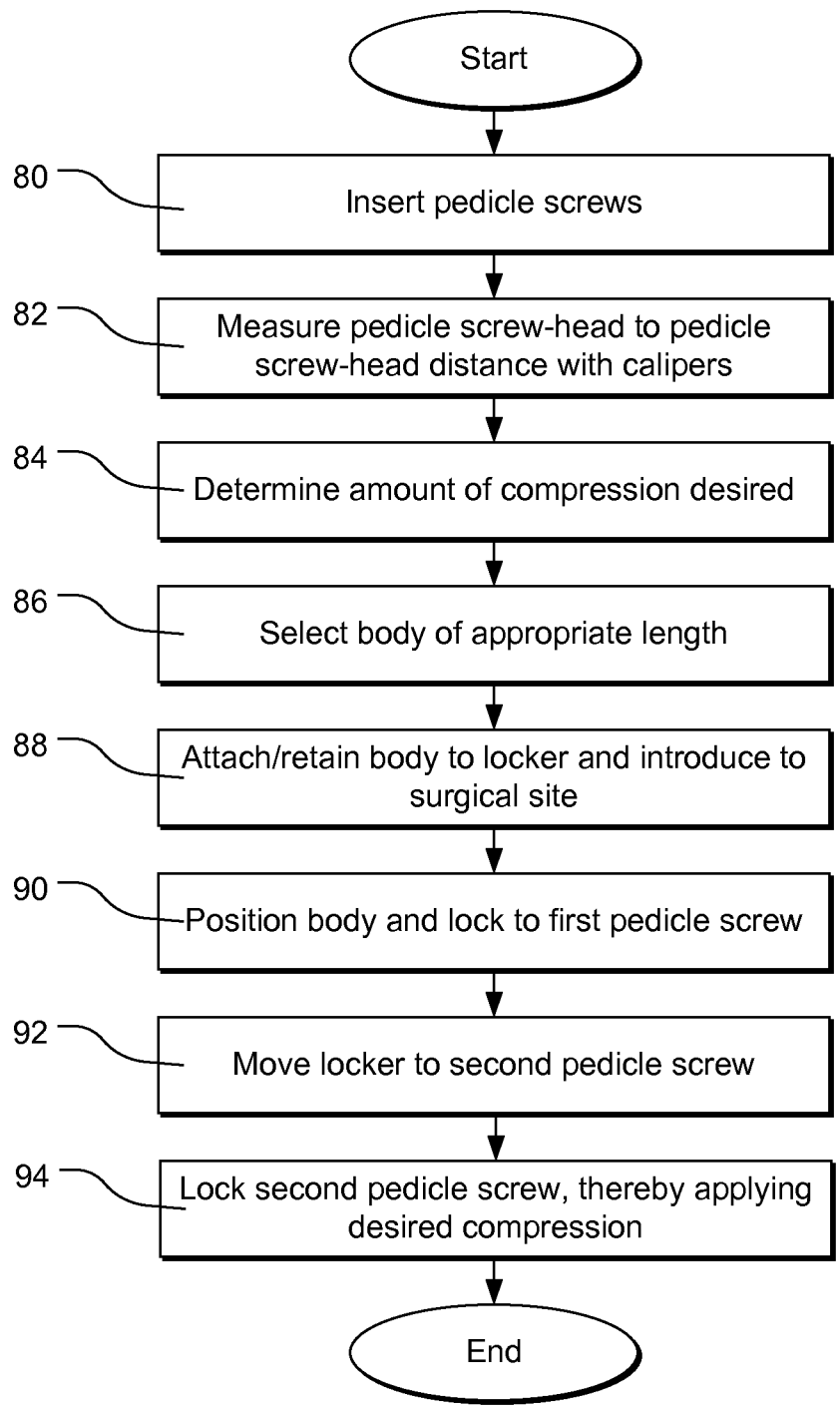
FIG. 16 shows an flow chart of an exemplary method for achieving compression with a press-fit surgical construct.
Figure 17:
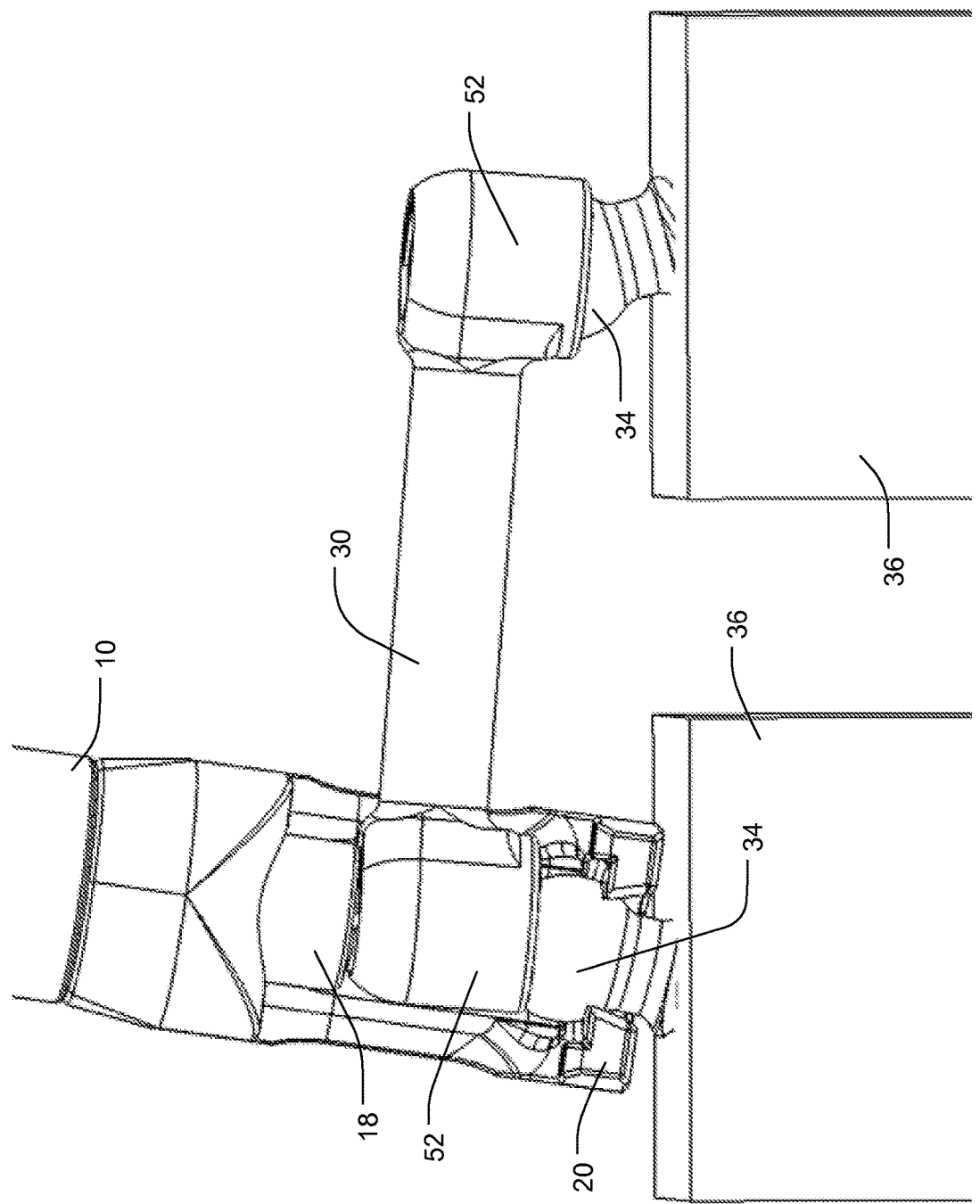
FIG. 17 depicts a perspective view of a late stage of the method of FIG. 16.

The intervertebral space can be compressed (decrease in intervertebral distance) without the use of a separate compressor instrument through the procedure outlined below and shown in FIGS. 16-17. The surgeon first inserts the pedicle screws to the desired depth at step 80. At step 82, the surgeon uses calipers to measure the pedicle screw-head to pedicle screw-head distance. The surgeon then determines the amount of compression desired at step 84, and selects a body 30 that is the corresponding amount shorter than the measured distance at step 86. For example, if the calipers measured a pedicle screw head to pedicle screw head distance of 34 mm, and 2 mm of compression is desired, the surgeon would select a 32 mm body 30 (e.g. a fixed-length rod of 32 mm). At step 88, the selected body 30 is then attached to and retained by the locker 10 in the manner discussed herein and is introduced to the surgical site at the first pedicle screw in the manner discussed above.

The surgeon then uses the locker to lock the body to the first screw head 34 at step 90. When the surgeon locks the first tulip body 52 of the body 30 to the first pedicle screw head 34, the surgeon may use the locker 10 to apply leverage to the body 30, partially mobilizing and compressing the spinal segment. At step 92, the surgeon then removes the locker 10 from the first pedicle screw and positions the locker 10 at the second pedicle screw as described above and as shown in FIG. 17. This step may involve steps of retaining the body 30 at the second pedicle screw in the manner discussed above, then positioning the screw-engaging tip 20 below the screw head 34 of the second pedicle screw, either sequentially or simultaneously. The surgeon then positions the second end of the body 30 so that it can be locked to the second pedicle screw head 34. Note in the depiction of FIG. 17 that the body 30 is shorter than the pre-lock distance between the heads 34 of the pedicle screws, and the second (left) pedicle screw is not yet aligned with the second (left) fixed-length rod coupler or tulip body 52.

At step 94, the surgeon uses the locker 10 to lock the second pedicle screw head 34 to the body 30. As the locker 10 presses the second tulip body 52 or fixed-length rod coupler onto the second pedicle screw head 34, the second pedicle screw 34 is pulled toward the second tulip body 34 or fixed-length rod coupler (which moves it closer to the first pedicle screw). Thus, locking the second pedicle screw to the body 30 or fixed-length rod completes the compression. In cadaveric testing, surgeons have been able to apply up to 6 mm of compression with this technique.

When using cylindrical pedicle screws 38 and screw balls 40, an alternate method is possible in which the first pedicle screw uses a cylindrical pedicle screw 38 and screw ball 40 in the unlocked assembled state. This allows the surgeon to manipulate the spine, with the first end in an assembled, but free moving condition. In this case, the surgeon selects the length of the body 30 or fixed-length rod as above (steps 80-86), then "snaps" the first tulip body 52 or fixed-length rod coupler onto the first cylindrical pedicle screw 38 into the unlocked assembled state. The surgeon "snaps" the second tulip body 52 or fixed-length rod coupler onto the second cylindrical pedicle screw 38 into the unlocked assembled state at the second end as above, thereby achieving the bulk of the desired compression, then returns and fully locks the first end and second end in the manner described herein, which finalizes the compression. Alternatively, the surgeon can lock the second end immediately after snapping the first end, and only needs move the locker 10 once more to lock the first end.

Figure 18:
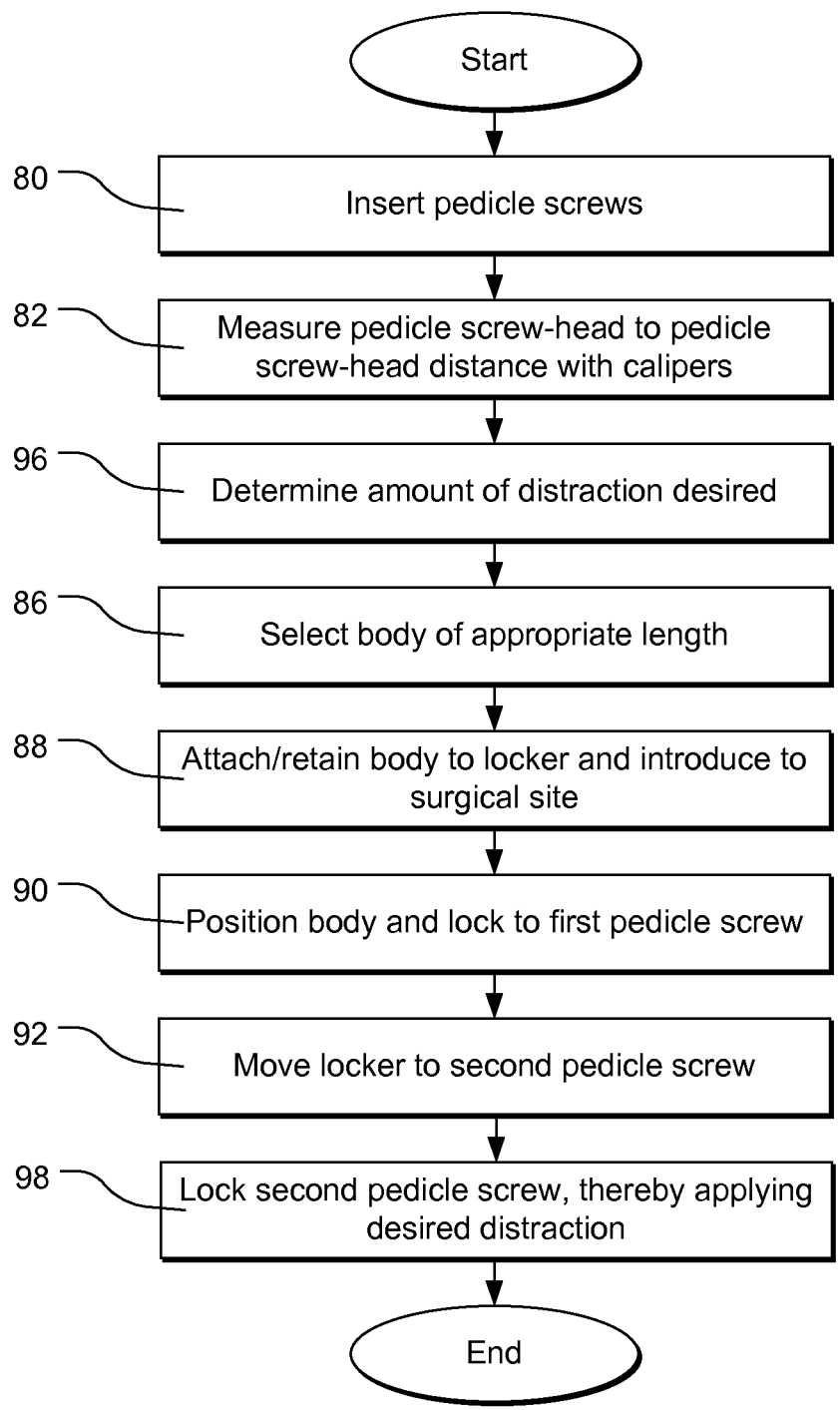
FIG. 18 shows an flow chart of an exemplary method for achieving distraction with a press-fit surgical construct.
Figure 19:
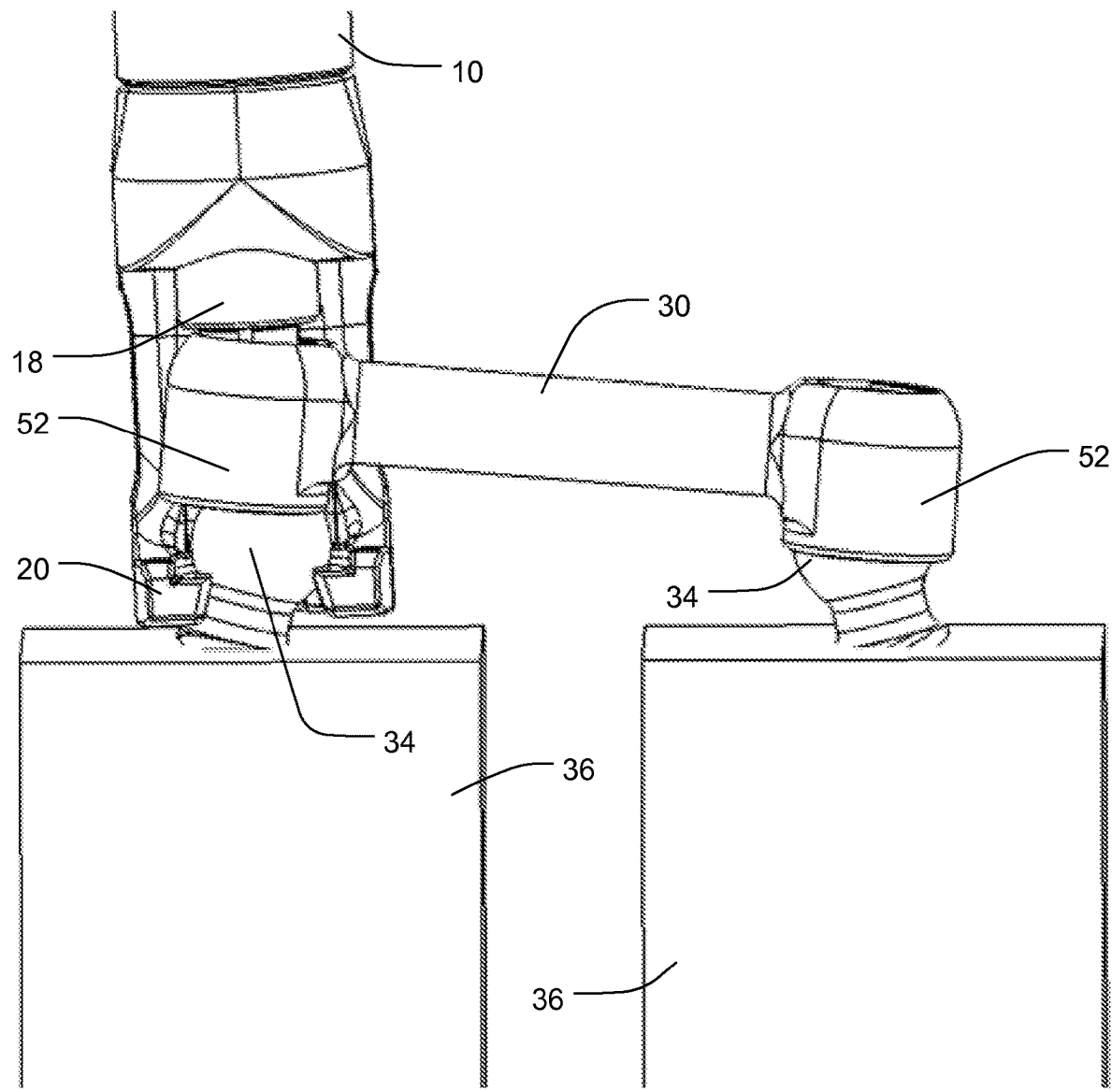
FIG. 19 depicts a perspective view of a late stage of the method of FIG. 18.

The intervertebral space can be distracted (increase in intervertebral distance) without the use of a separate distractor instrument through the procedure outlined below and shown in FIGS. 18-19. Many steps of the process are identical to or similar to the process of compression, so the surgeon needs little to no additional training to achieve both compression or distraction. The surgeon first inserts the pedicle screws to the desired depth at step 80. At step 82, the surgeon uses calipers to measure the pedicle screw-head to pedicle screw-head distance. The surgeon then determines the amount of distraction desired at step 96, and selects a body 30 that is the corresponding amount longer than the measured distance at step 86. For example, if the calipers measured a pedicle screw head to pedicle screw head distance of 34 mm, and 2 mm of distraction is desired, the surgeon would select a 36 mm body 30 (e.g. a fixed-length rod of 36 mm). At step 88, the selected body 30 is then attached to and retained by the locker 10 in the manner discussed herein and is introduced to the surgical site at the first pedicle screw in the manner discussed above.

The surgeon then uses the locker to lock the body to the first screw head 34 at step 90. When the surgeon locks the first tulip body 52 of the body 30 to the first pedicle screw head 34, the surgeon may use the locker 10 to apply leverage to the body 30, partially mobilizing and distracting the spinal segment. At step 92, the surgeon then removes the locker 10 from the first pedicle screw and positions the locker 10 at the second pedicle screw as described above and as shown in FIG. 19. This step may involve steps of retaining the body 30 at the second pedicle screw in the manner discussed above, then positioning the screw-engaging tip 20 below the screw head 34 of the second pedicle screw, either sequentially or simultaneously. The surgeon then positions the second end of the body 30 so that it can be locked to the second pedicle screw head 34. Note in the depiction of FIG. 19 that the body 30 is longer than the pre-lock distance between the heads 34 of the pedicle screws, and the second (left) pedicle screw is not yet aligned with the second (left) fixed-length rod coupler or tulip body 52.

At step 98, the surgeon uses the locker 10 to lock the second pedicle screw head 34 to the body 30. As the locker 10 presses the second tulip body 52 or fixed-length rod coupler onto the second pedicle screw head 34, the second pedicle screw 34 is pulled toward the second tulip body 34 or fixed-length rod coupler (which moves it further from the first pedicle screw). Thus, locking the second pedicle screw to the body 30 or fixed-length rod completes the distraction. In cadaveric testing, surgeons have been able to apply up to 6 mm of distraction with this technique.

When using cylindrical pedicle screws 38 and screw balls 40, an alternate method is possible in which the first pedicle screw uses a cylindrical pedicle screw 38 and screw ball 40 in the unlocked assembled state. This allows the surgeon to manipulate the spine, with the first end in an assembled, but free moving condition. In this case, the surgeon selects the length of the body 30 or fixed-length rod as above (steps 80, 82, 96, and 86), then "snaps" the first tulip body 52 or fixed-length rod coupler onto the first cylindrical pedicle screw 38 into the unlocked assembled state. The surgeon "snaps" the second tulip body 52 or fixed-length rod coupler onto the second cylindrical pedicle screw 38 into the unlocked assembled state at the second end as above, thereby achieving the bulk of the desired distraction, then returns and fully locks the first end and second end in the manner described herein, which finalizes the distraction. Alternatively, the surgeon can lock the second end immediately after snapping the first end, and only needs move the locker 10 once more to lock the first end.

Figure 20:
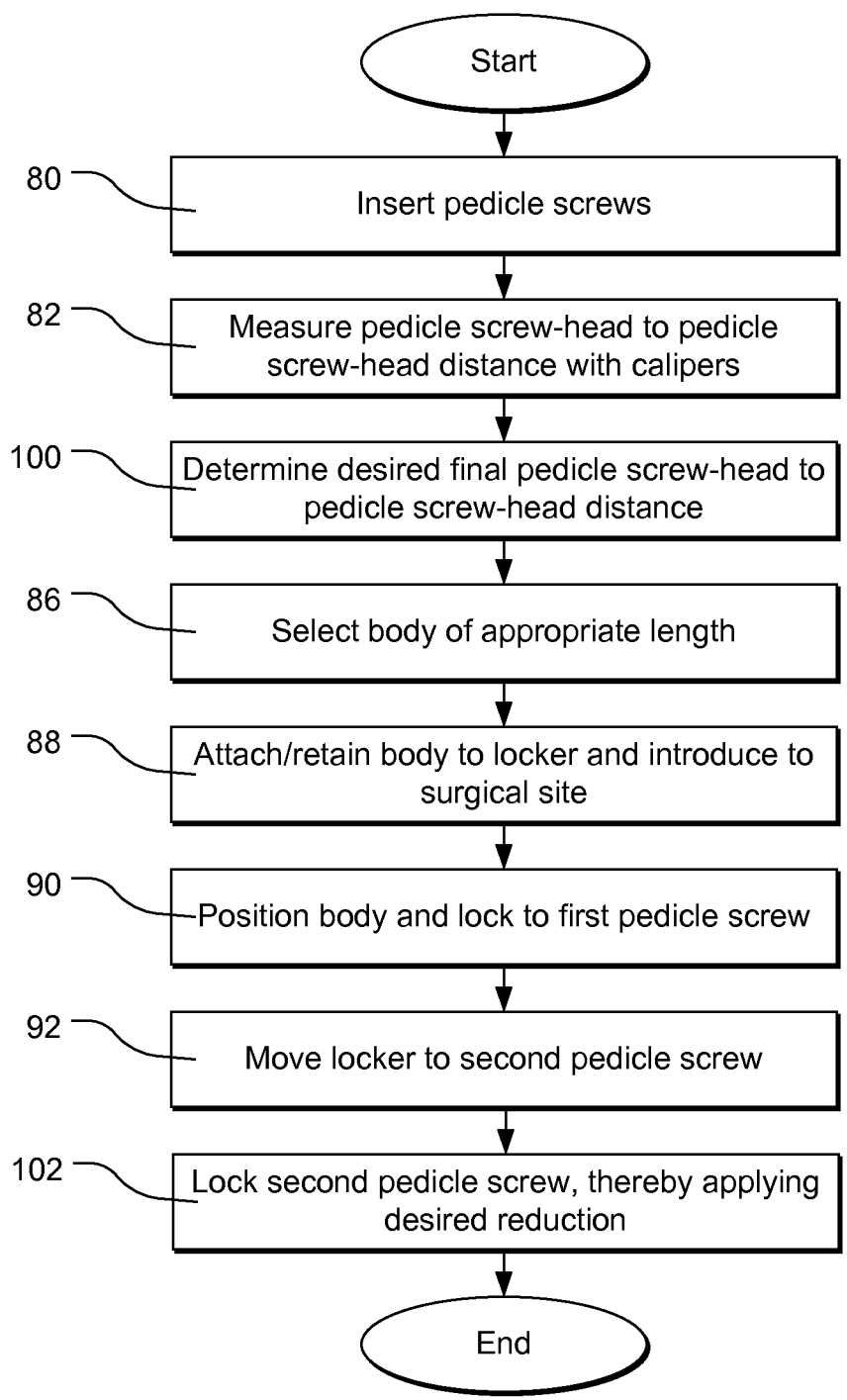
FIG. 20 shows an flow chart of an exemplary method for achieving reduction with a press-fit surgical construct.
Figure 21:
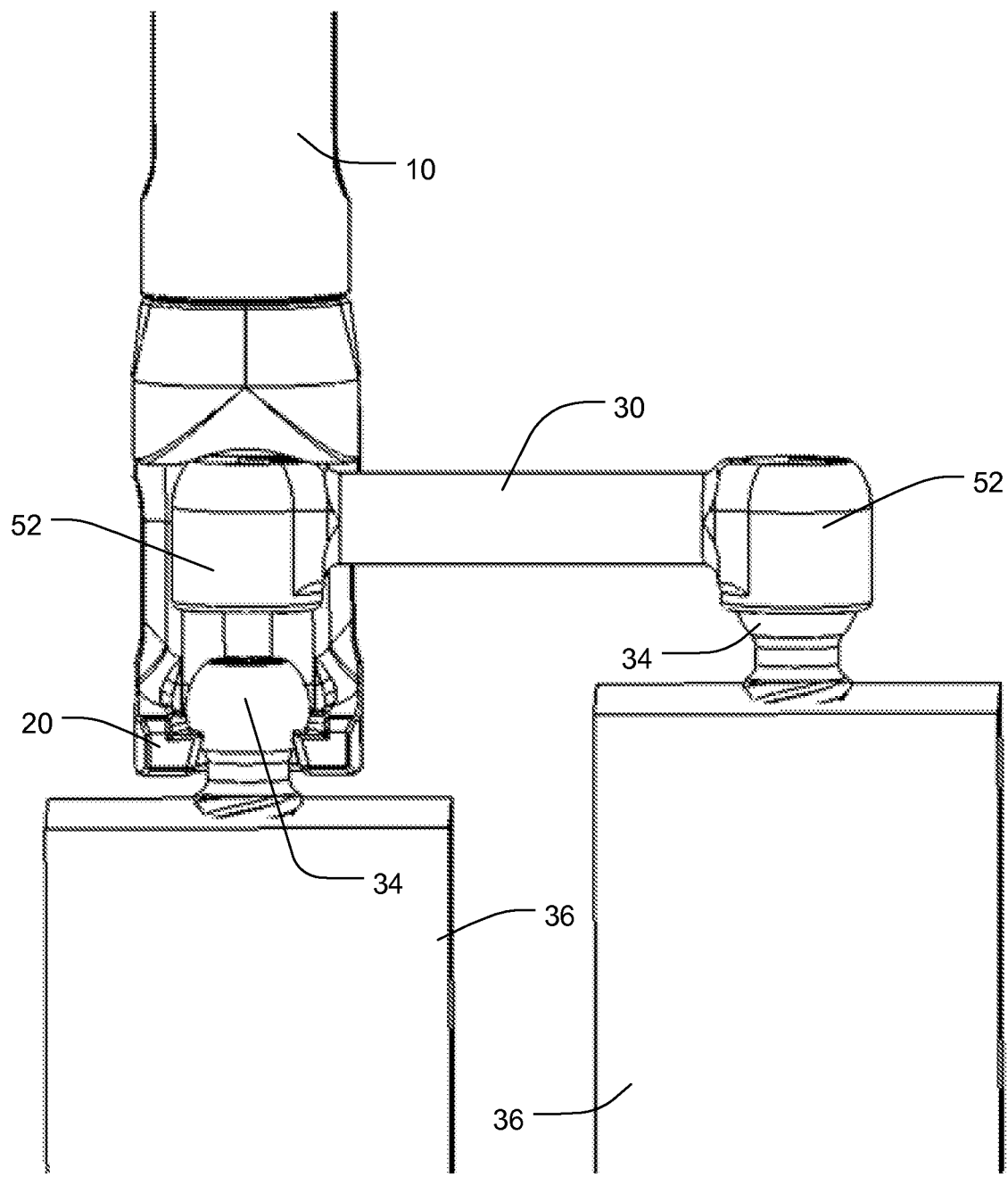
FIG. 21 depicts a perspective view of a late stage of the method of FIG. 20.

A spondylolisthesis can be reduced without the use of a separate persuader/reducer instrument through the procedure outlined below and shown in FIGS. 20-21. Many steps of the process are identical to or similar to the process of compression or the process of distraction, so the surgeon needs little to no additional training to achieve reduction along with compression or distraction. The surgeon first inserts the pedicle screws to the desired depth at step 80. At step 82, the surgeon uses calipers to measure the pedicle screw-head to pedicle screw-head distance. The surgeon then determines the desired pedicle screw-head to pedicle screw-head distance after reduction of the spondylolisthesis at step 100, and selects a body 30 that corresponds to that anticipated distance at step 86. At step 88, the selected body 30 is then attached to and retained by the locker 10 in the manner discussed herein and is introduced to the surgical site at the first pedicle screw (the pedicle screw at the vertebral body not to be reduced) in the manner discussed above.

The surgeon then uses the locker to lock the body to the first screw head 34 at step 90. When the surgeon locks the first tulip body 52 of the body 30 to the first pedicle screw head 34, the surgeon uses the locker 10 to position the second end of the body above the head 34 of the second pedicle screw, which is in the vertebral body to be reduced, at a distance corresponding to the desired amount of reduction, as shown in FIG. 21 (the locker 10 has already been repositioned in FIG. 21). When the first tulip body 52 is locked to the first screw head 34 in this fashion, the body 30 forms a cantilevered structure above the second pedicle screw. At step 92, the surgeon then removes the locker 10 from the first pedicle screw and positions the locker 10 at the second pedicle screw as described above and as shown in FIG. 21. This step may involve steps of retaining the body 30 at the second pedicle screw in the manner discussed above, then positioning the screw-engaging tip 20 below the screw head 34 of the second pedicle screw, either sequentially or simultaneously.

At step 102, the surgeon uses the locker 10 to lock the second pedicle screw head 34 to the body 30. As the locker 10 presses the second tulip body 52 or fixed-length rod coupler onto the second pedicle screw head 34, the second pedicle screw 34 is pulled toward the second tulip body 34 or fixed-length rod coupler (which reduces the second pedicle screw and the associated vertebral body). Thus, locking the second pedicle screw to the body 30 or fixed-length rod completes the reduction. Up to 8 mm of reduction can be applied with this technique; however, greater reduction could be achieved by mobilizing the spinal segment with the locker 10 by first engaging the screw with the screw-engaging tip 20, then manually pulling up on the second pedicle screw prior to engaging the body 30 and locking the second tulip body 52 or coupler in the manner described.

Figure 22:
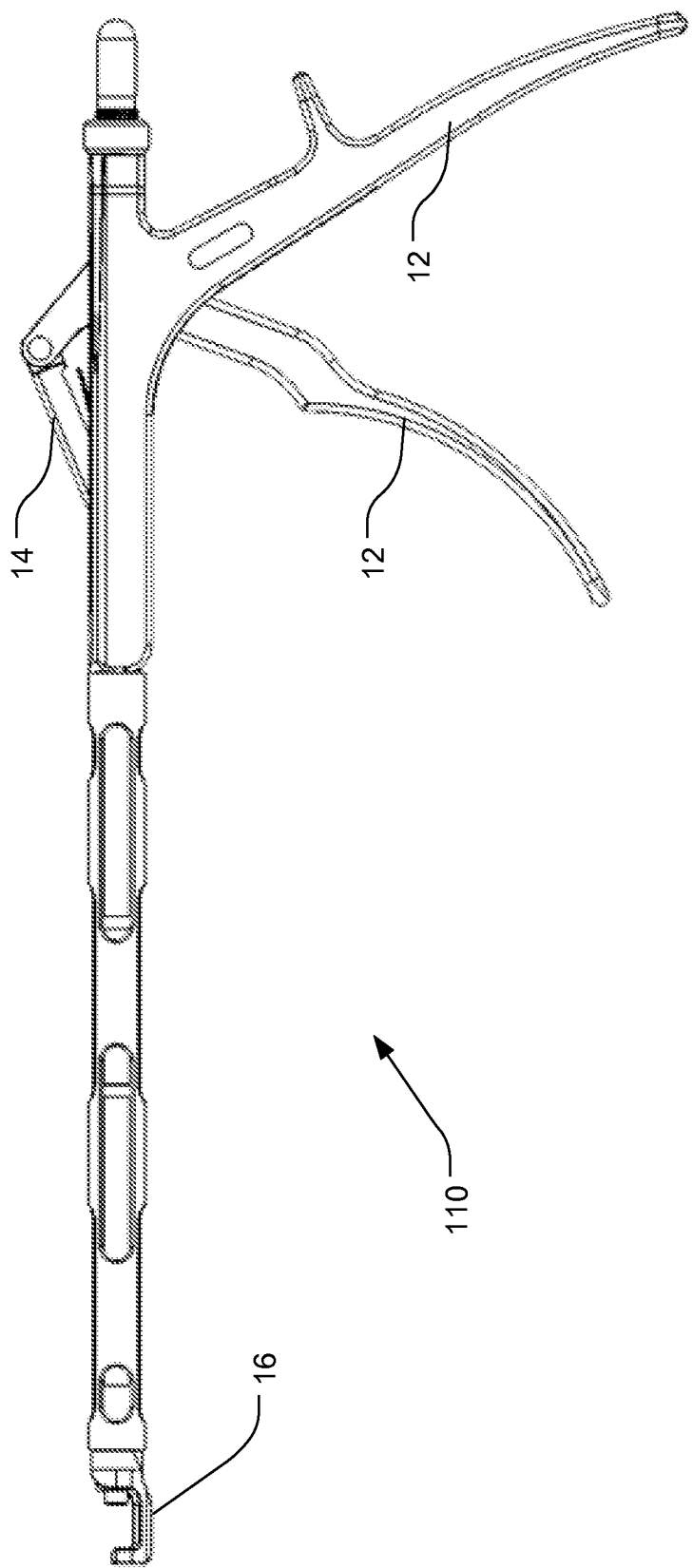
FIG. 22 shows a side view of an unlocker in an unactuated state.
Figure 23:
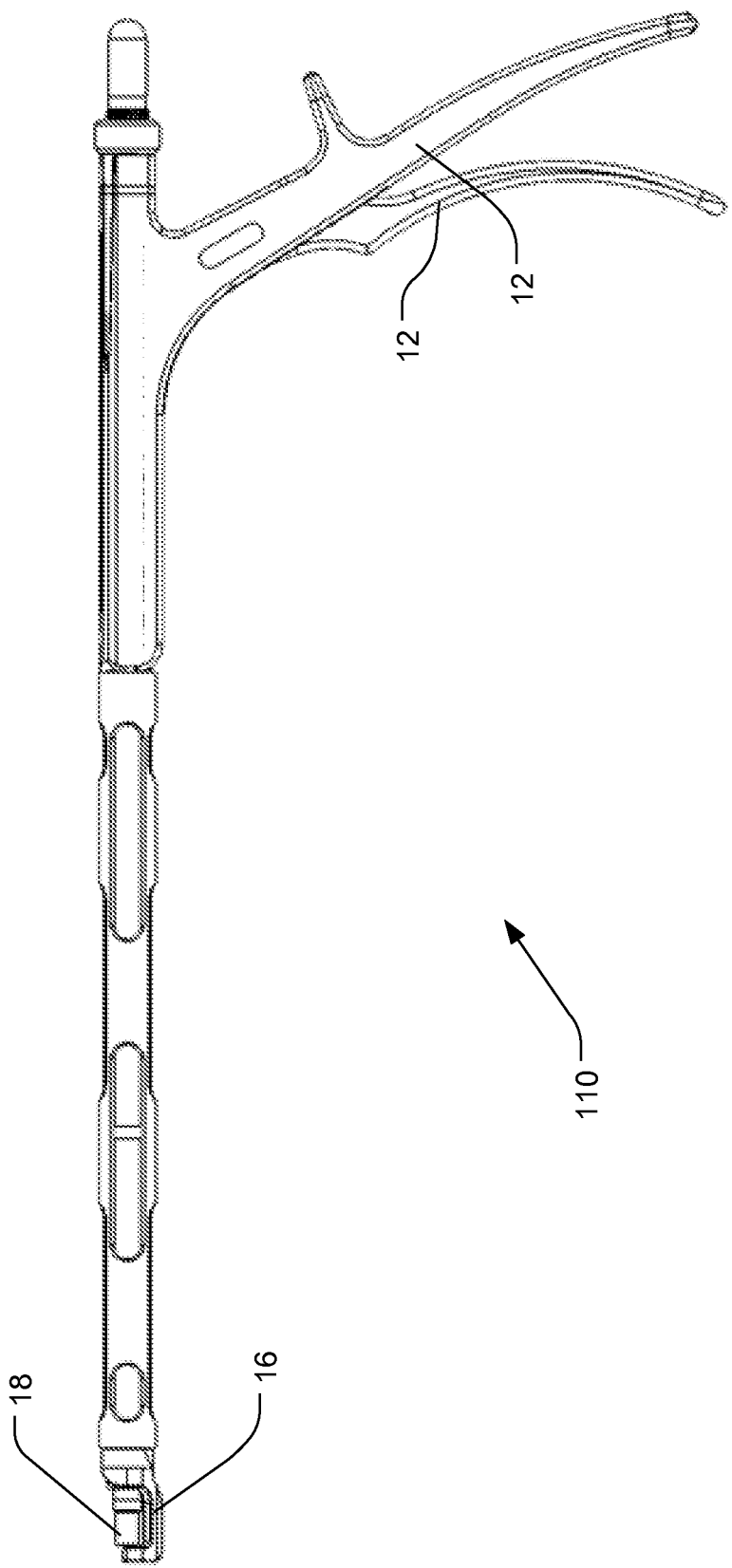
FIG. 23 shows a side view of an unlocker in an unactuated state.

As discussed above, the act of locking the pedicle screw head 34 to the body 30 creates a strong coupling between the pedicle screw and the body 30 that is not subject to decoupling during normal use or operation of the components, and that cannot be decoupled without the use of tools or under normal physiologic loads of the spine. Nevertheless, as decoupling is at times necessary, an unlocker tool, which may take a similar pistol shape as the pistol shape of the locker 10 may be provided to unlock the body 30 from the pedicle screw. Thus, an unlocker 110 as shown in FIGS. 22-23 may be utilized to unlock the body 30 from the pedicle screw by pressing the pedicle screw head 34 out of the tulip body 52 or coupler.

The unlocker 110 is in many ways similar to the locker 10: it includes handles 12 and a linkage 14, as well as a construct-engaging tip 16. There are some differences: the rod is longer to allow the rod tip 18 to push the pedicle screw out of the tulip head 52. Additionally, the rod tip 18 need not have a retention feature to retain the body thereon 30, although it may still retain the retention feature. The embodiment of FIGS. 22-23 does not have a retention feature. Additionally, the opening at the construct-engaging tip 16 is more similar to the body-engaging tip 62 than the screw-engaging tip 30, such that the construct-engaging tip 16 engages the body 30 (e.g. tulip body 52) while allowing the screw head 34 to pass through freely during unlocking.

Figure 24:
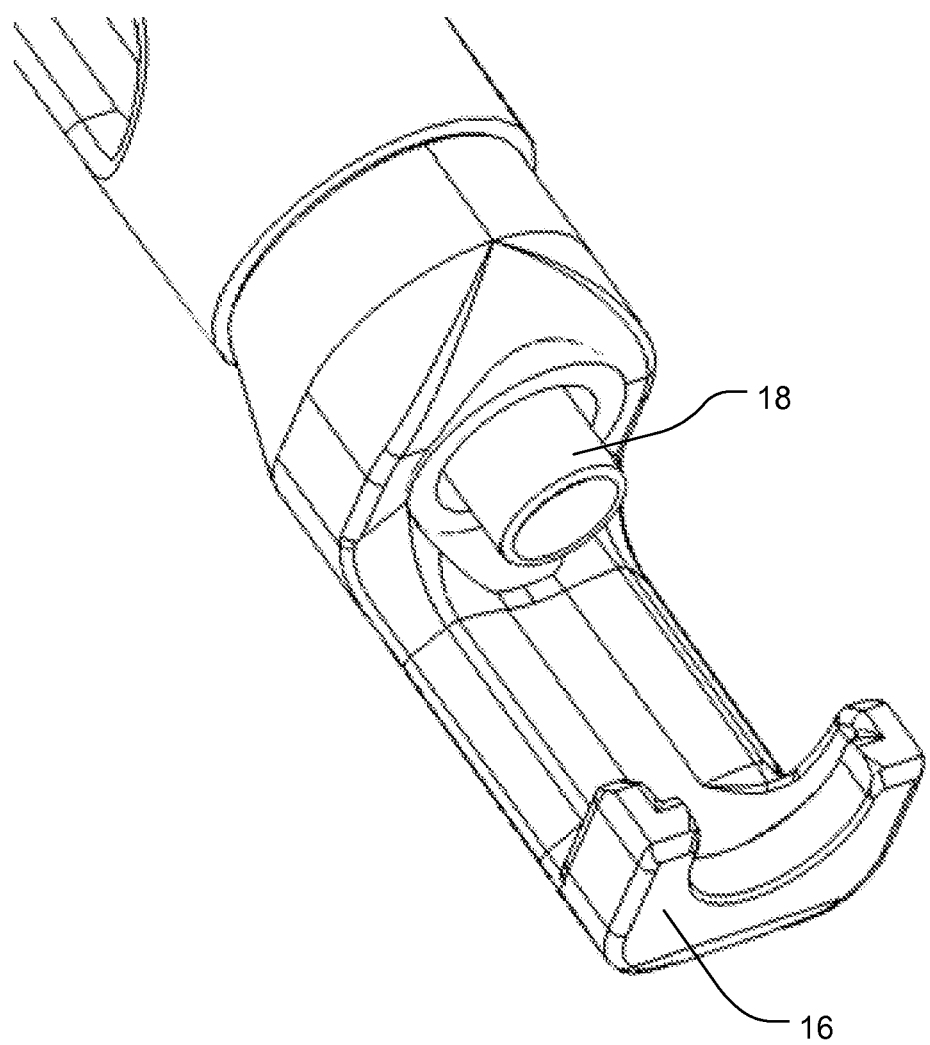
FIGS. 24-29 show various views of a distal tip of the unlocker of FIGS. 22-23 with and without associated surgical constructs, illustrating the uncoupling functionality of the unlocker.
Figure 25:
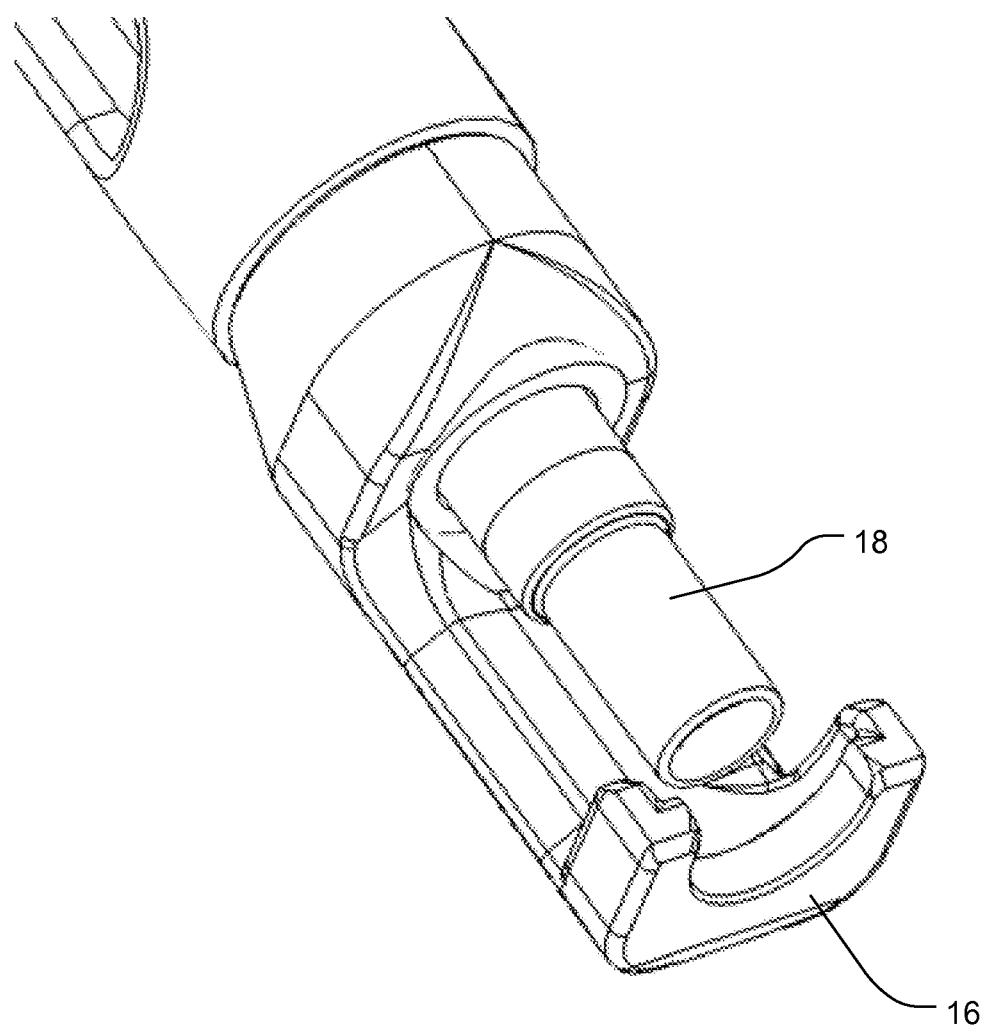
Figure 26:
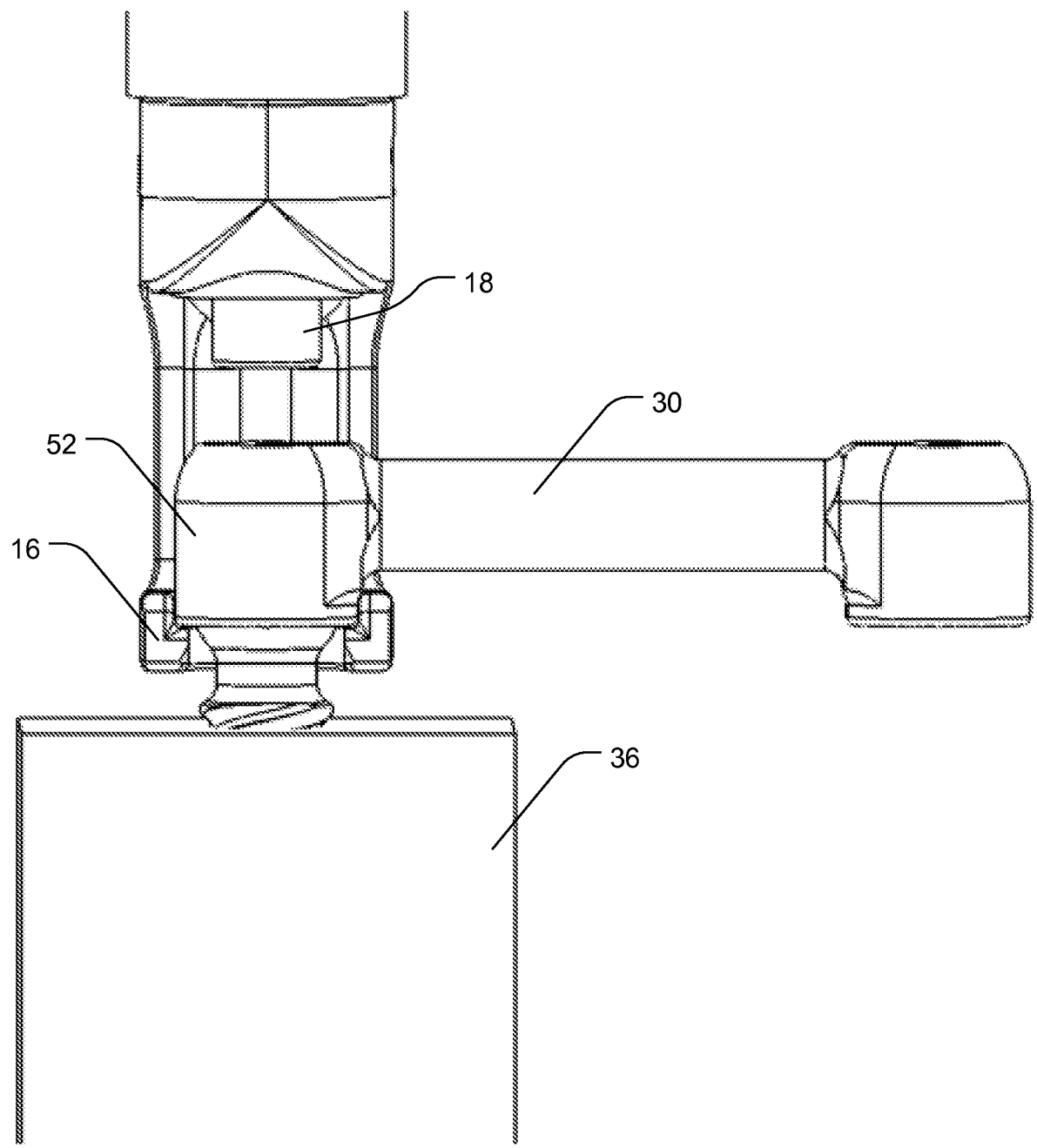
Figure 27:
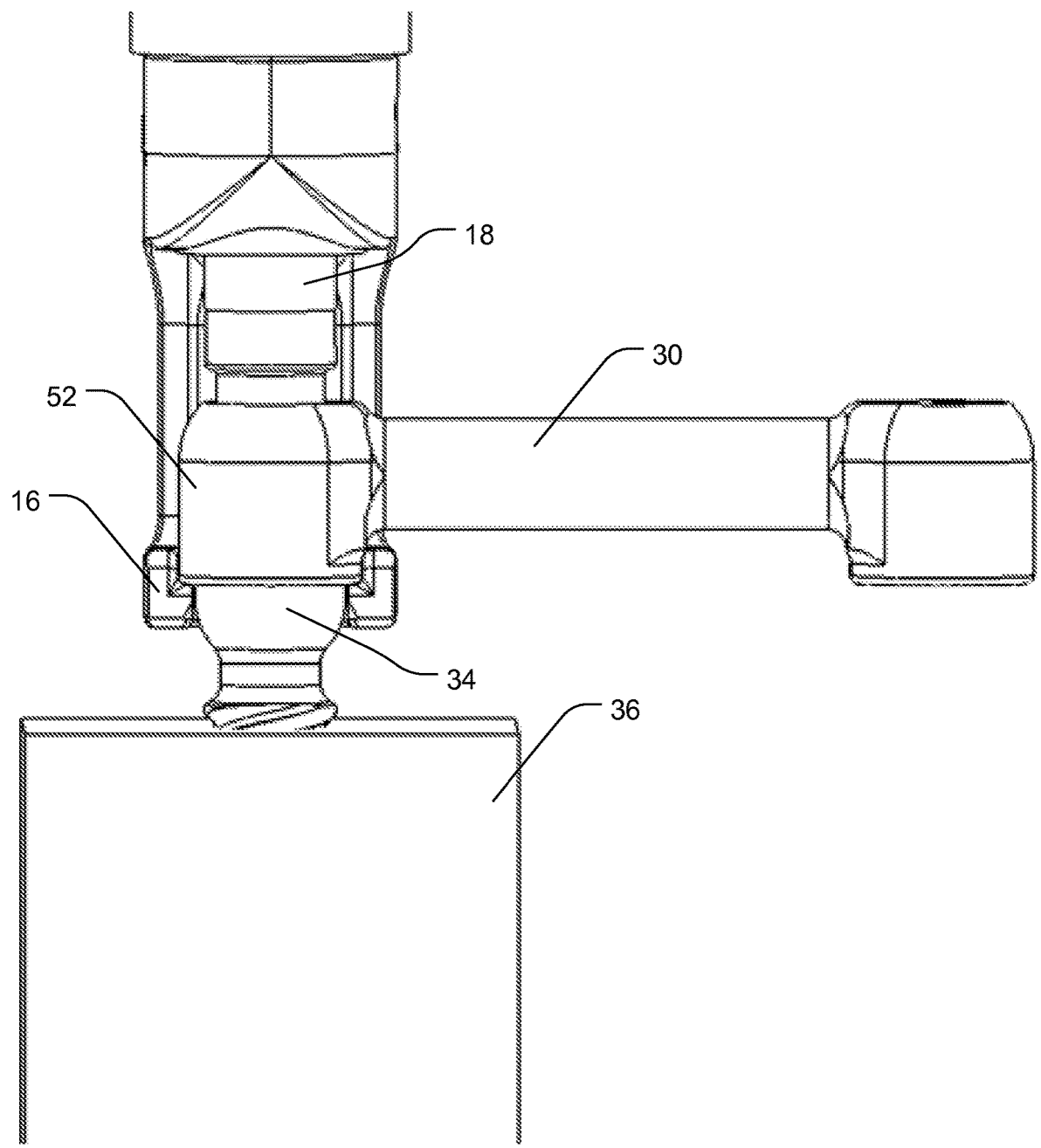
Figure 28:
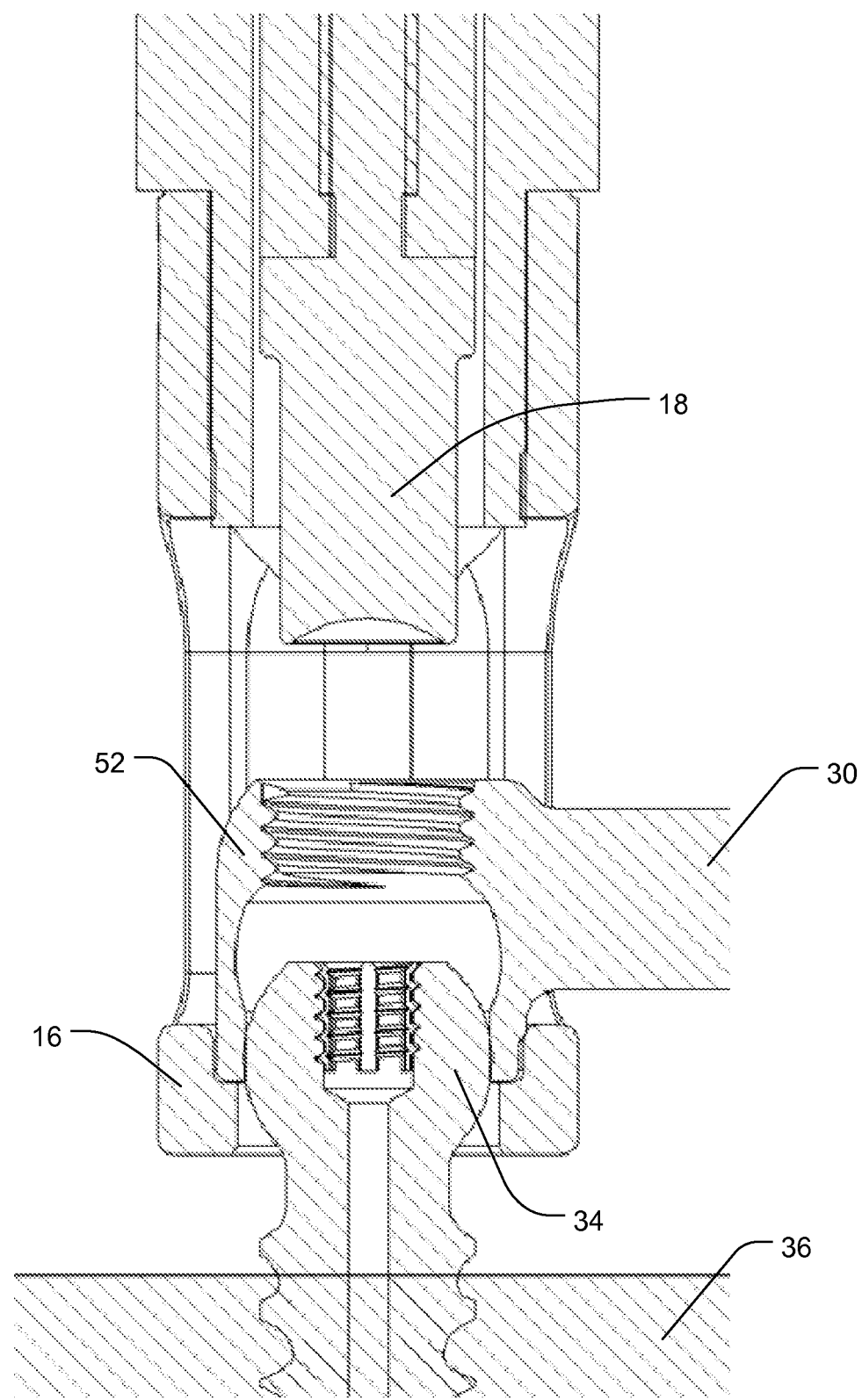
Figure 29:
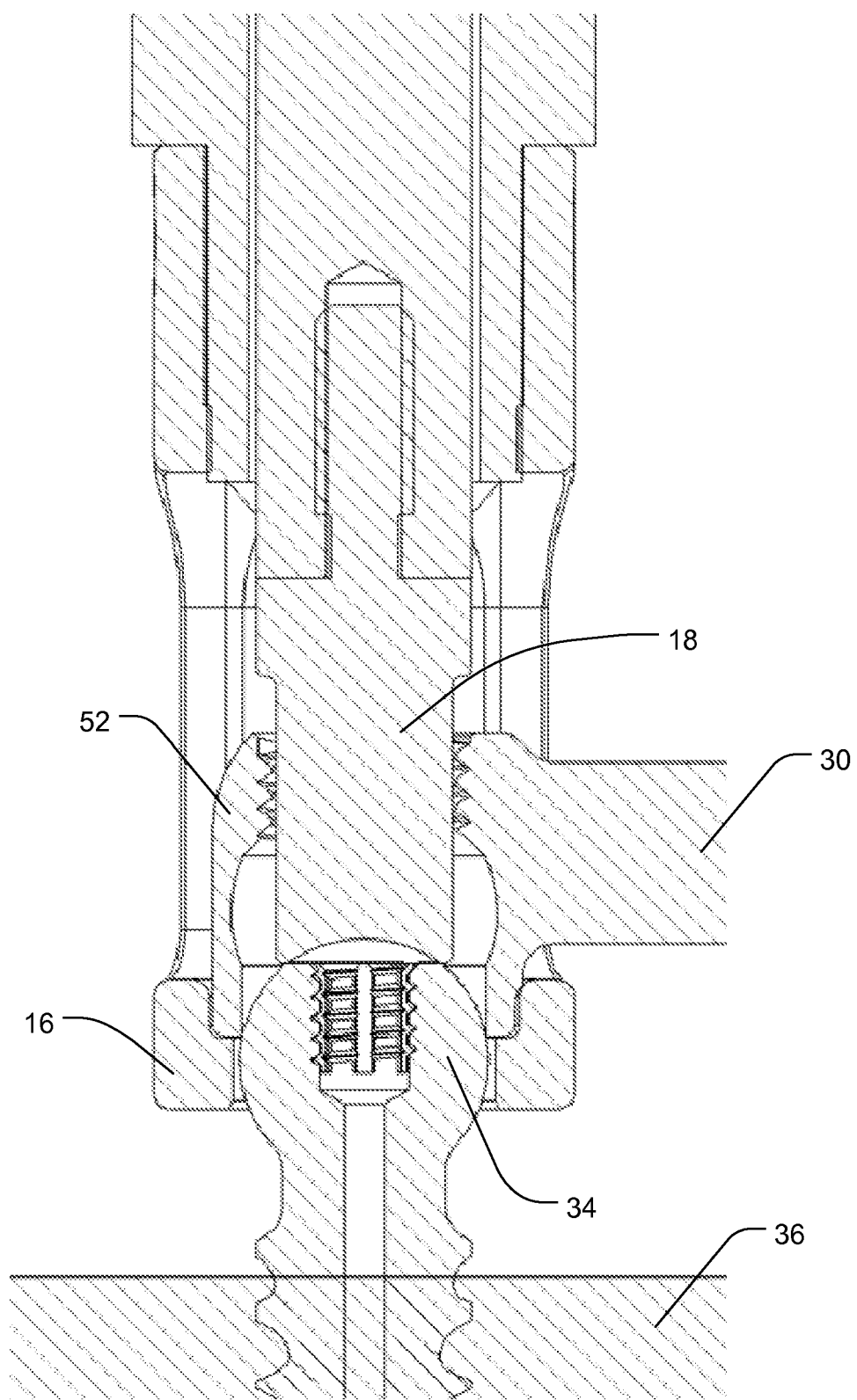

The procedure for using the unlocker 110 is as follows. Place the distal end of the unlocker (the construct-engaging tip 16) under the body 30/tulip head 52/coupler to be unlocked. Fully actuate the instrument, pushing the pedicle screw head 34 out of the body 30/tulip head 52/coupler. After unlocking the second body 30/tulip head 52/coupler in the same fashion, continue to apply pressure to the handle 12/trigger to retain the body 30 as the instrument is removed from the surgical site. FIGS. 24-25 show the distal end of the unlocker 110 in unactuated and actuated positions, respectively. FIGS. 26-29 show representative use of the unlocker 110 in perspective and cutaway views to unlock the body 30 from a pedicle screw.

In certain of the illustrated embodiments, the second or upper bore 32 has been illustrated as being threaded. Where the second or upper bore 32 is threaded, a threaded locker and/or unlocker may be used (in conjunction with any appropriate or needed anti-torque devices such as those commonly known in the art), including a threaded set screw, to supply a locking and/or unlocking force to the pedicle screw. The use of a threaded locker and/or unlocker provides an alternative option for delivering locking and/or unlocking force to the pedicle screw relative to the body.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiment(s) of the invention. It will be apparent to those of ordinary skill in the art that numerous modifications can be made without departing from the principles and concepts of the invention as set forth in the examples. The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A device for coupling a surgical construct to a pedicle screw, the device comprising:
   an elongate body comprising a primary axis;
   a handle having a proximal end attached to the elongate body and extending away from the elongate body at a proximal end of the elongate body and at an acute angle as taken from the proximal end of the elongate body such that a distal end of the handle is radially spaced away from the primary axis of the elongate body a distance adapted to accommodate a hand of a surgeon between the elongate body and the distal end of the handle;
   a rod running through the elongate body;
   a force-multiplying linkage operatively connected to a proximal end of the rod, the force-multiplying linkage having a first position extending beyond the elongate body on a side of the elongate body opposite the handle and a second position in which the force-multiplying linkage is advanced distally and substantially contained within the elongate body;
   a trigger connected to the rod through the force-multiplying linkage, the trigger extending away from the elongate body proximate the handle at an obtuse angle as taken from the proximal end of the elongate body and on a same side of the elongate body as the handle when in a non-actuated state; and
   a construct-engaging tip at a distal end of the elongate body and adapted to contact and engage a distal spherical surface of a head of a pedicle screw in situ in a pedicle and secure the pedicle screw against distal movement;
   wherein actuating the trigger causes the rod to move within the elongate body toward the construct-engaging tip such that a distal end of the rod protrudes from the elongate body a distance sufficient to apply a force to a first component of the surgical construct while the construct-engaging tip applies a directionally opposite force to the pedicle screw.

2. A device as recited in claim 1, wherein the construct-engaging tip comprises an open-sided aperture sized to accept a shaft of a pedicle screw therethrough.

3. A device as recited in claim 1, wherein the distal end of the rod comprises a surgical construct retaining feature.

4. A device as recited in claim 3, wherein the surgical construct retaining feature comprises a rigid post surrounded by a plurality of flexible segments.

5. A device as recited in claim 4, wherein the rod and the rigid post are cannulated.

6. A device as recited in claim 1, wherein the construct-engaging tip is adapted to secure a head of a pedicle screw and wherein the rod is adapted to apply force to a tulip body of a surgical construct to thereby couple the tulip body to the head of the pedicle screw via a press fit.

7. A device as recited in claim 1, wherein the rod is cannulated.

8. A device as recited in claim 1, wherein the trigger extends away from the primary axis of the elongate body in a generally proximal direction when the trigger is fully actuated.

9. A device as recited in claim 1, wherein a portion of the handle extending away from the primary axis of the elongate body and a portion of the trigger extending away from the primary axis of the elongate body are each sized to receive a hand or hands of a surgeon to permit the surgeon to actuate the trigger by squeezing the trigger toward the handle.

10. The device as recited in claim 1, wherein the handle extends away from the elongate body at an angle of approximately 60 degrees as taken from the proximal end of the elongate body and wherein the trigger extends away from the elongate body at an angle of approximately 120 degrees as taken from the proximal end of the elongate body when in the non-actuated state.

11. A device for coupling a surgical construct to a pedicle screw, the device comprising:
    an elongate body comprising a primary axis and a proximal end;
    a first handle having a structure sized to receive a hand or hands of a surgeon extending away from the elongate body at an acute angle as take from the proximal end of the elongate body such that a distal end of the handle is radially spaced away from the primary axis of the elongate body a distance adapted to accommodate a hand of a surgeon between the elongate body and the distal end of the handle;
    a rod running through the elongate body and comprising a surgical construct retaining feature on a distal end thereof;
    a force-multiplying linkage, the force-multiplying linkage comprising a crank slider operatively connected to a proximal end of the rod;
    a trigger connected to the rod through the crank slider of the force-multiplying linkage, the trigger being formed as a second handle sized to receive a hand or hands of a surgeon and extending away from the elongate body proximate the first handle at an obtuse angle as taken from the proximal end of the elongate body and on a same side of the elongate body as the handle when in a non-actuated state; and
    a construct-engaging tip at a distal end of the elongate body and adapted to contact and engage a distal spherical surface of a head of pedicle screw in situ in a pedicle and secure the pedicle screw against distal movement relative to the construct-engaging tip;
    wherein actuating the trigger causes the rod to move within the elongate body toward the construct-engaging tip such that the distal end of the rod protrudes from the elongate body a distance sufficient to apply a force to a tulip body of the surgical construct while the construct-engaging tip applies a directionally opposite force to the pedicle screw.

12. A device as recited in claim 11, wherein the construct-engaging tip comprises an open-sided aperture sized to accept a shaft of a pedicle screw therethrough.

13. A device as recited in claim 11, wherein the surgical construct retaining feature comprises a rigid post surrounded by a plurality of flexible segments.

14. A device as recited in claim 13, wherein the rod and the rigid post are cannulated.

15. A device as recited in claim 11, wherein the rod is adapted to apply force to a tulip body of a surgical construct to thereby couple the tulip body to the head of the pedicle screw via a press fit.

16. A device for coupling a surgical construct to a pedicle screw, the device comprising:
- an elongate body comprising a primary axis and a proximal end;
- a first handle with a hand-receiving portion sized to receive a hand of a surgeon, the hand-receiving portion attached to and extending away from the elongate body at an acute angle as taken from the proximal end of the elongate body such that a distal end of the handle is radially spaced away from the primary axis of the elongate body a distance adapted to accommodate the hand of the surgeon between the elongate body and the distal end of the handle;
- a rod running through the elongate body and comprising a surgical construct retaining feature on a distal end thereof;
- a force-multiplying linkage comprising a crank slider affixed on one end to a proximal end of the rod, wherein the force-multiplying linkage has a first position extending beyond the elongate body on a side of the elongate body opposite the first handle and a second position in which the force-multiplying linkage is advanced distally and substantially contained within the elongate body
- a trigger connected to the rod through the force-multiplying linkage, the trigger being formed as a second handle with a hand-receiving portion sized to receive the hand of the surgeon, the hand-receiving portion of the trigger extending away from the elongate body proximate the first handle at an obtuse angle as taken from the proximal end of the elongate body and on a same side of the elongate body as the hand-receiving portion of the first handle; and
- a construct-engaging tip at a distal end of the elongate body and adapted to contact and engage a distal spherical surface of a head of a pedicle screw in situ in a pedicle and secure the pedicle screw against distal movement relative to the construct-engaging tip;
- wherein actuating the trigger causes the rod to move within the elongate body toward the construct-engaging tip such that the distal end of the rod protrudes from the elongate body a distance sufficient to apply a force to a tulip body of the surgical construct while the construct-engaging tip applies a directionally opposite force to the pedicle screw.

17. The device as recited in claim 16, wherein the construct-engaging tip comprises an open-sided aperture sized to accept a shaft of a pedicle screw therethrough.

18. The device as recited in claim 16, wherein the surgical construct retaining feature comprises a rigid post surrounded by a plurality of flexible segments.

19. The device as recited in claim 18, wherein the rod and the rigid post are cannulated.

20. The device as recited in claim 16, wherein the rod is adapted to apply force to a tulip body of a surgical construct to thereby couple the tulip body to the head of the pedicle screw via a press fit.

* * * * *